(12) United States Patent
Hodgson et al.

(10) Patent No.: US 10,314,616 B2
(45) Date of Patent: Jun. 11, 2019

(54) IVF EGG COLLECTION CHAMBER

(71) Applicants: LABMAN AUTOMATION LTD., North Yorkshire (GB); UNIVERSITY OF NEWCASTLE UPON TYNE, Newcastle Upon Tyne, Tyne and Wear (GB); NEWCASTLE UPON TYNE HOSPITALS NHS FOUNDATION TRUST, Newcastle Upon Tyne, Tyne and Wear (GB)

(72) Inventors: Robert Hodgson, Leeds (GB); Alison Murdoch, Newcastle Upon Tyne (GB)

(73) Assignees: Labman Automation Ltd., North Yorkshire (GB); University of Newcastle Upon Tyne, Newcastle Upon Tyne, Tyne and Wear (GB); Newcastle Upon Tyne Hospitals NHS Foundation Trust, Newcastle Upon Tyne, Tyne and Wear (GB)

( * ) Notice: Subject to any disclaimer, the term of this patent is extended or adjusted under 35 U.S.C. 154(b) by 592 days.

(21) Appl. No.: 14/894,551

(22) PCT Filed: May 30, 2014

(86) PCT No.: PCT/GB2014/051653
§ 371 (c)(1),
(2) Date: Nov. 30, 2015

(87) PCT Pub. No.: WO2014/191757
PCT Pub. Date: Dec. 4, 2014

(65) Prior Publication Data
US 2016/0113680 A1    Apr. 28, 2016

(30) Foreign Application Priority Data
May 31, 2013 (GB) .................................. 1309766.2

(51) Int. Cl.
*A61B 17/435*    (2006.01)
*A61D 19/04*    (2006.01)
*C12M 1/26*    (2006.01)

(52) U.S. Cl.
CPC ............ *A61B 17/435* (2013.01); *A61D 19/04* (2013.01); *C12M 33/14* (2013.01)

(58) Field of Classification Search
CPC .... A61B 17/425; A61B 17/435; A61D 19/04; C12M 33/14
See application file for complete search history.

(56) References Cited

U.S. PATENT DOCUMENTS

| 4,563,172 A | 1/1986 | Ferguson |
| 4,781,706 A * | 11/1988 | Suzuki .................. A61D 19/04 128/897 |

(Continued)

FOREIGN PATENT DOCUMENTS

| EP | 0489403 A2 | 6/1992 |
| JP | H04329965 A | 11/1992 |

(Continued)

OTHER PUBLICATIONS

International Search Report dated Sep. 18, 2014 for PCT/GB2014/051653.

(Continued)

*Primary Examiner* — Carrie R Dorna
(74) *Attorney, Agent, or Firm* — Abel Schillinger, LLP

(57) ABSTRACT

The present invention relates to egg chambers for use in collection, inspection and selection of eggs for in vitro fertilization (IVF) procedures. The egg chamber, in use, provides an effectively closed and fluid filled system which minimizes the environmental changes that a harvested egg is exposed to, thus maximizing viability. The egg chamber comprises a vessel which can be made airtight, comprising (Continued)

Figure 1:
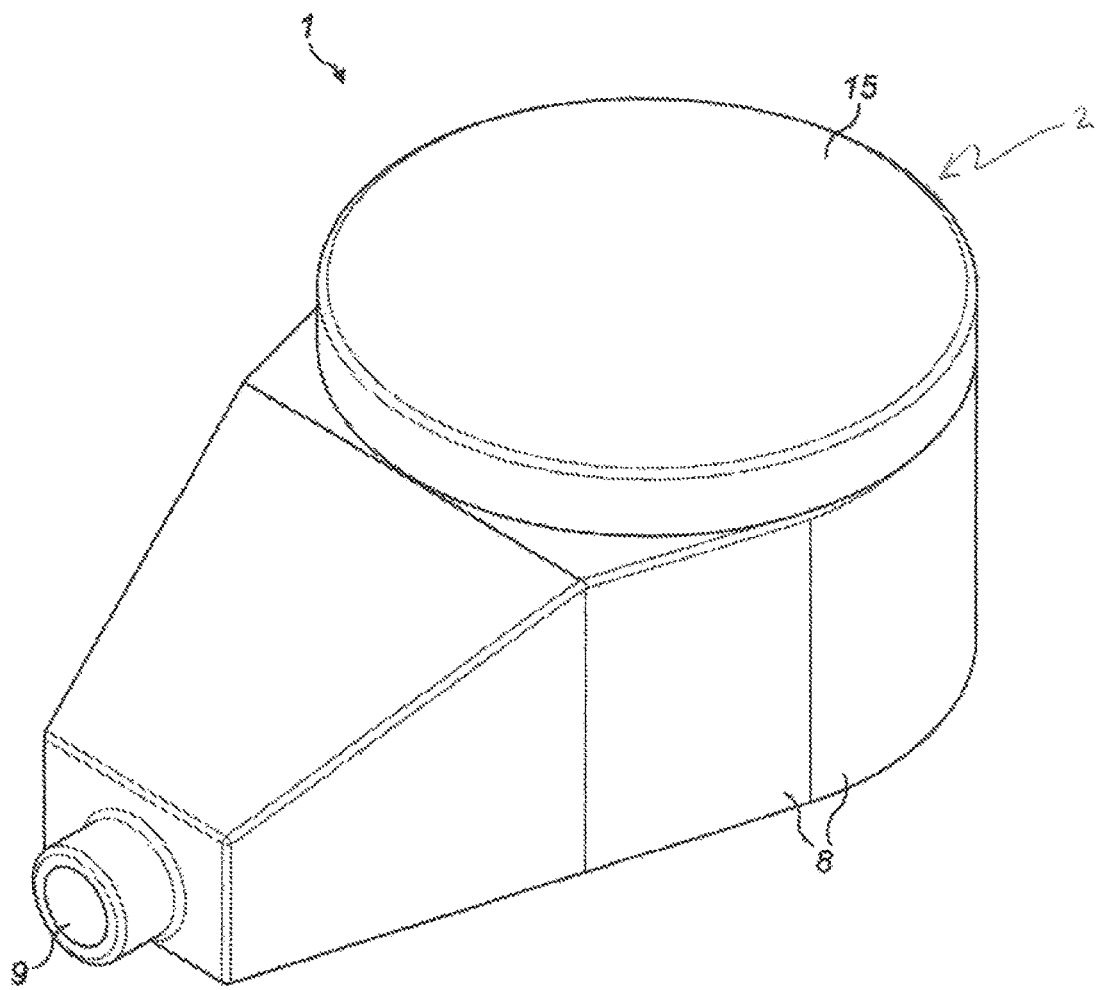

at least one side wall, an upper wall and a lower wall, at least a portion of the upper wall being transparent and at least a portion of the lower wall being light permeable; a first inlet with a sealable port; a first outlet with a sealable port; a filter with a pore size appropriate for egg collection disposed within the vessel between the first inlet and the first outlet and configured to separate the vessel into a first internal chamber and a second internal chamber.

53 Claims, 18 Drawing Sheets

(56) References Cited

U.S. PATENT DOCUMENTS

| | | | | |
|---|---|---|---|---|
| 5,042,979 | A | | 8/1991 | Anderson et al. |
| 5,223,151 | A | * | 6/1993 | Rojas ............ A61D 19/04 128/897 |
| 5,273,527 | A | * | 12/1993 | Schatz ............ A61B 10/0291 604/164.13 |
| 5,505,716 | A | | 4/1996 | Simmet et al. |
| 5,514,119 | A | * | 5/1996 | Curtis ............ A61D 19/04 600/563 |
| 6,050,935 | A | * | 4/2000 | Ranoux ............ A61B 17/435 600/33 |
| 6,673,008 | B1 | | 1/2004 | Thompson et al. |
| 2003/0236488 | A1 | | 12/2003 | Novak |
| 2004/0092791 | A1 | * | 5/2004 | Bateman ............ A61B 17/435 600/34 |
| 2008/0154095 | A1 | * | 6/2008 | Stubkjaer ............ A61M 3/0258 600/156 |
| 2014/0038283 | A1 | * | 2/2014 | Jose ............ C12M 47/02 435/325 |

FOREIGN PATENT DOCUMENTS

| | | |
|---|---|---|
| WO | WO9006990 A1 | 6/1990 |
| WO | WO2004108011 A1 | 12/2004 |

OTHER PUBLICATIONS

Nelson, et al. Predicting Live Birth, Preterm Delivery, and Low Birth Weight in Infants Born from In Vetro Fertilisation: A Prospective Study of 144,018 Treatment Cycles.

Claassens, et al., "Optimizing sensitivity of the human sperm motility assay for embryo toxicity testing." Hum. Reprod. (2000) 15 (7): 1586-1591 doi:10.1093/humrep/15.7.1586, http://www.ncbi.nlm.nih.gov/pubmed/10875871.

* cited by examiner

IVF EGG COLLECTION CHAMBER

This is a 371 of International Patent Application Ser. No. PCT/GB2014/051653, filed on May 30, 2014, and claims priority from GB Patent Application Serial No. 1309766.2, filed on May 31, 2013, both applications being incorporated herein by reference in their entireties.

The present invention relates to egg chambers for use in collection, inspection and selection of eggs for in vitro fertilisation (IVF) procedures and a fluid pump system thereof. The egg chamber, in use, provides an effectively closed and fluid filled system which minimises the environmental changes that a harvested egg is exposed to, thus maximising viability. The fluid pump system provides a unique and advantageous semi-automated system allowing for an efficient and safe retrieval of the egg(s).

In vitro fertilisation (IVF) is a process where an ovum or egg is fertilised outside of the body or outside of the organism or animal in which it is naturally found. The technique is used for human fertility treatment and variations are used for other animals, either for veterinary purposes or for other commercial purposes. In humans, IVF is primarily used as a treatment for infertility, but it is also carried out on couples who carry a genetic mutation, but are not infertile (e.g. pre-implantation genetic diagnosis). IVF involves removing one or more ova (eggs) from a woman's ovaries, then combining with sperm in an appropriate fluid within a laboratory setting in order to allow fertilisation of the ova to occur. One or more of the fertilised ova are then transferred back into a woman's uterus. It is typical that the process includes a number of additional steps to try to maximise the chance of a successful pregnancy, for example ovarian hyperstimulation, and specific culture and selection techniques. However, it is appreciated that there are still aspects of the process that reduce the chances of a successful pregnancy occurring, some of which occur during the collection of the ova or eggs. In particular, it is understood by those skilled in the art that exposing the ova or eggs to environmental or physiological change, such as changes in temperature (Wang et al., 2001), dissolved O2 and pH (Wilding et al 1998; Daya et al., 1988; Cockburn et al 1973, or exposure to volatile organic compounds (VOC) (Legro et al., 2010) can be detrimental to egg viability.

The number of patients undergoing IVF treatment in the UK has increased by ~6.5% each year over the last 5 years with 57,652 treatments performed in 2010. Despite increased experience, the number of babies born per treatment remains relatively low at only 25.2%. Evidence suggests that this is mainly due to the quality of the embryos; generally considered to be an inherent insurmountable human problem. However, our experience in the development and utilisation of an enclosed controlled system for fertilising and culturing embryos indicates that the number of babies born can be improved (increased implantation rate from 19.8% to 32.8%) (Hyslop et al., 2012).

Egg quality is the main determinant of outcome (Scott M. Nelson, Debbie A. Lawlor Predicting Live Birth, Preterm Delivery, and Low Birth Weight in Infants Born from In Vitro Fertilisation: A Prospective Study of 144,018 Treatment Cycles). The development potential of the egg can very easily be damaged by the culture environment e.g. temperature, pH and toxic factors in the air. Current IVF processes do not provide optimum environmental conditions as they expose the egg/embryo to the external environment. Nonetheless they have been accepted worldwide as being the only practical option.

Figure 3:
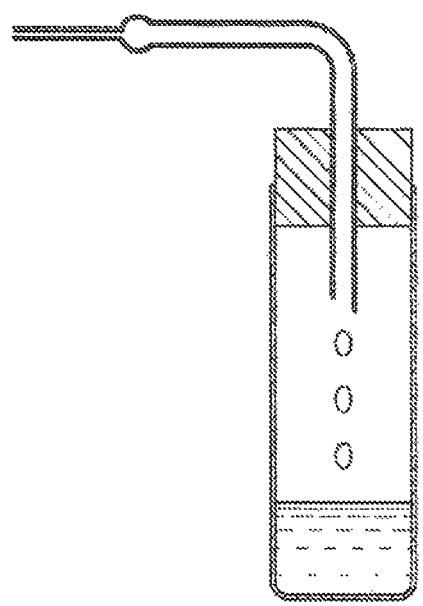

State of the art techniques for obtaining human ova or eggs during the IVF process involve aspiration of the fluid in the ovarian follicles via a needle passed through the top of the vagina under ultrasound guidance. A diagram of this prior art collection apparatus is shown in FIG. 3. The oocyte-cumulus complex is pulled from the follicle wall when the fluid is aspirated through the needle. The aspiration is controlled by suction via a foot pedal. The needle is connected via tubing to a bung (shown in FIG. 3), which can be inserted into the top of a test tube. During an egg retrieval procedure, it is typical for up to 10 test tubes of follicular fluid to be collected. When one test tube is full, the bung is removed and transferred to the next empty test tube, and the full test tube is sealed with a cap and placed on a hot block. The collection procedure is typically carried out in theatre with the patient under sedation. The follicular fluid containing the eggs is the passed from the clinician to an embryologist at the IVF lab (often transferred via a closed hatch) where the eggs are processed by an embryologist. In the IVF lab this involves transferring the tubes into a laminar flow hood or a Class II hood or an Isolator. The caps are removed from the test tube and the contents poured into a culture vessel which is placed on a heated microscope stage. The dish is then agitated/swirled and viewed through the microscope to identify the eggs. The eggs are picked up with a pipette, placed in medium to "rinse" them, and then placed in a culture vessel containing culture medium under oil. The culture vessels with the eggs are then kept in specialized IVF incubators under carefully controlled environmental conditions.

Figure 5:
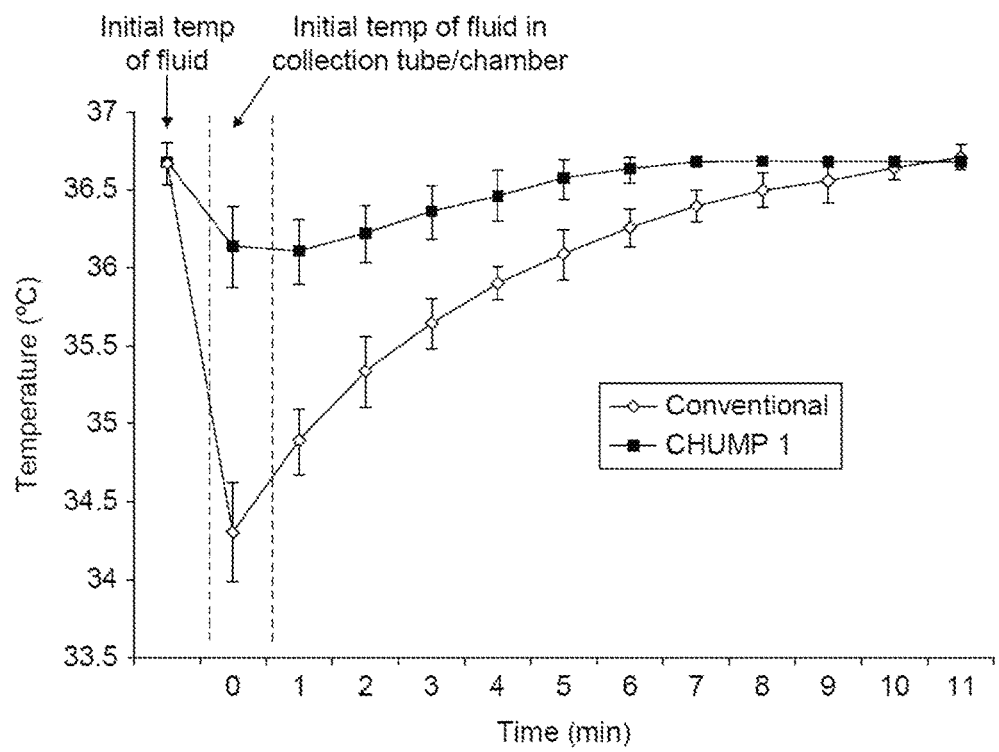

There are several limitations to the current process for egg retrieval. Firstly, heat loss occurs as the eggs are removed from the 37° C. environment of the patient, travel along the needle and tubing, and are collected in the test tube. The hot block in which the test tubes are stored during the procedure does not achieve a consistent temperature. As multiple test tubes are used and the bung is simply transferred from test tube to test tube during the procedure air enters the test tubes. As the same bung is used this can also lead to cross contamination and heat loss (FIG. 5). Further heat loss occurs as the eggs are processed by the embryologist, i.e. as the follicular fluid is transferred from the test tube to the culture vessel, as the culture dish is swilled to locate the eggs, during the time taken for the embryologist to identify the eggs, and during the process of transferring the eggs to a culture well under oil.

Figure 6:
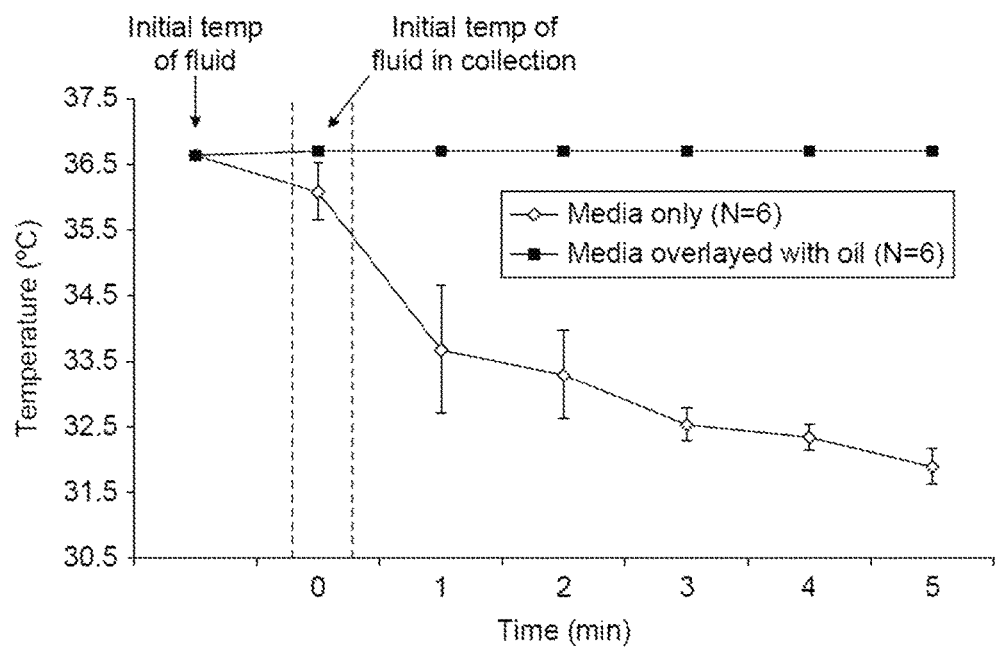
Figure 7A:
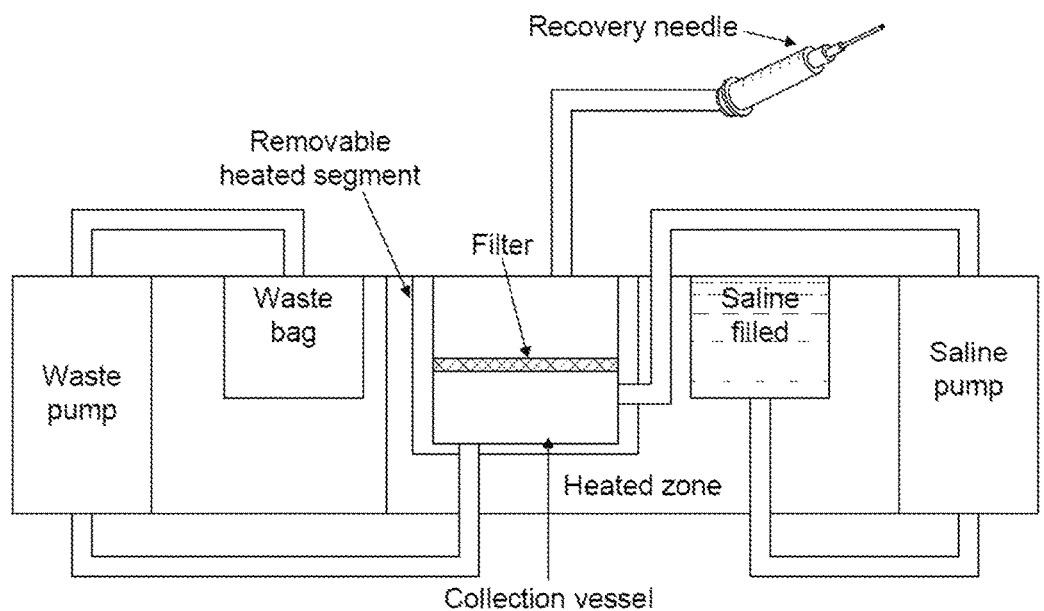
Figure 7B:
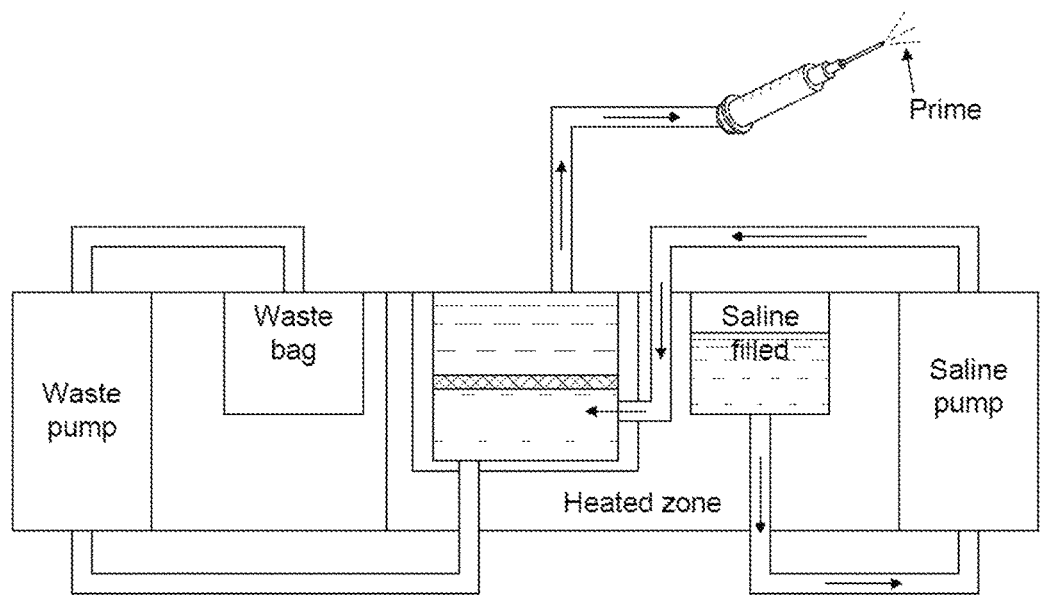
Figure 7C:
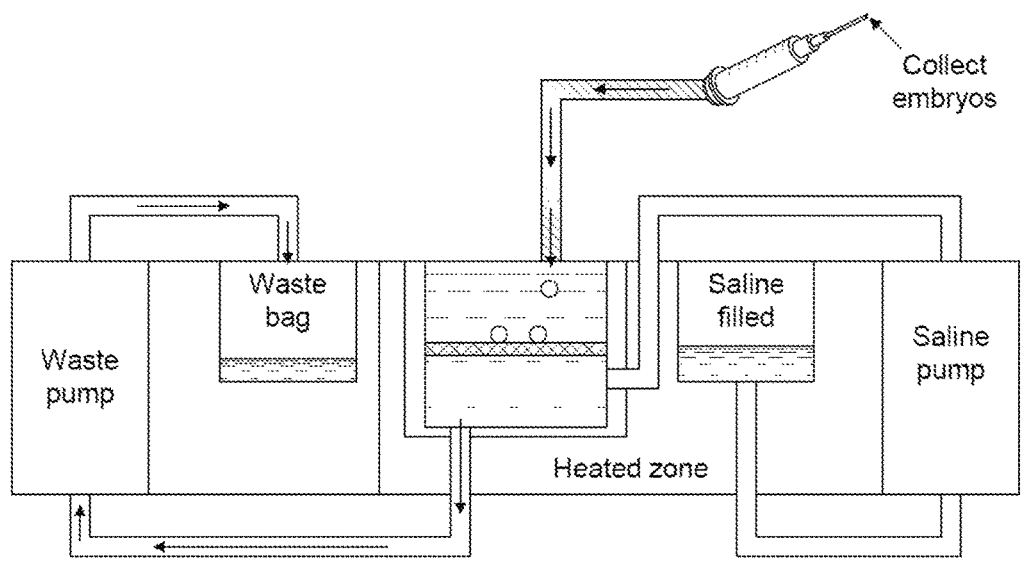
Figure 7D:
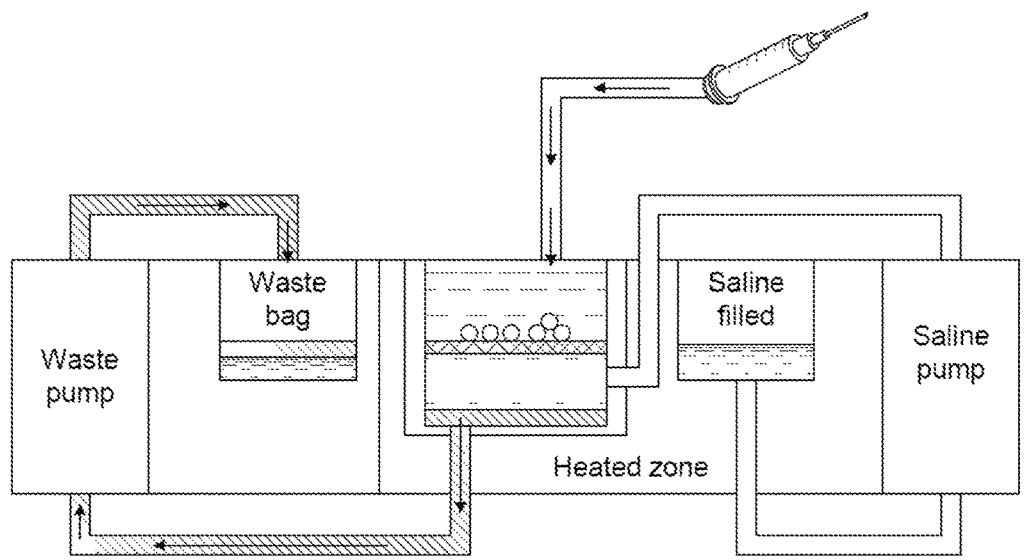
Figure 7E:
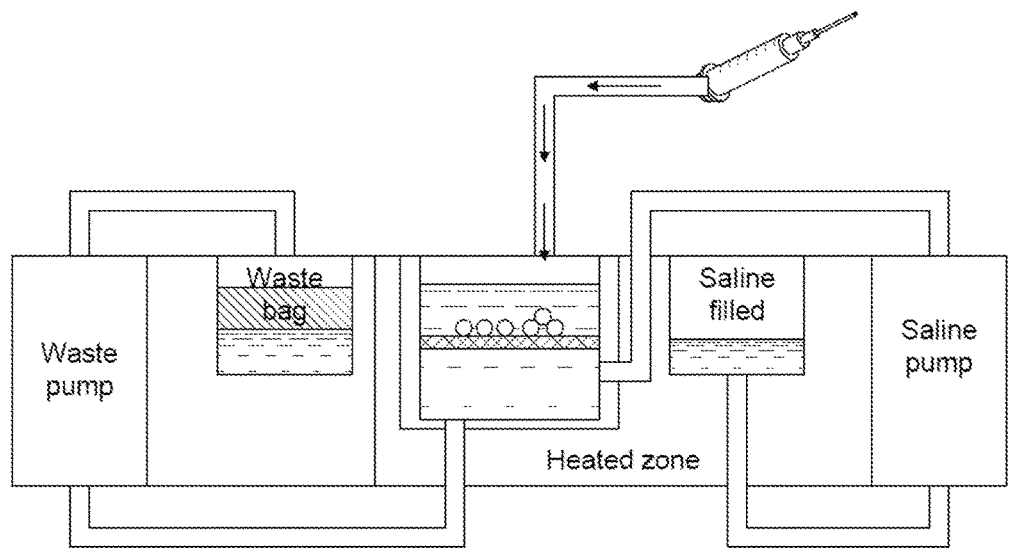
Figure 7F:
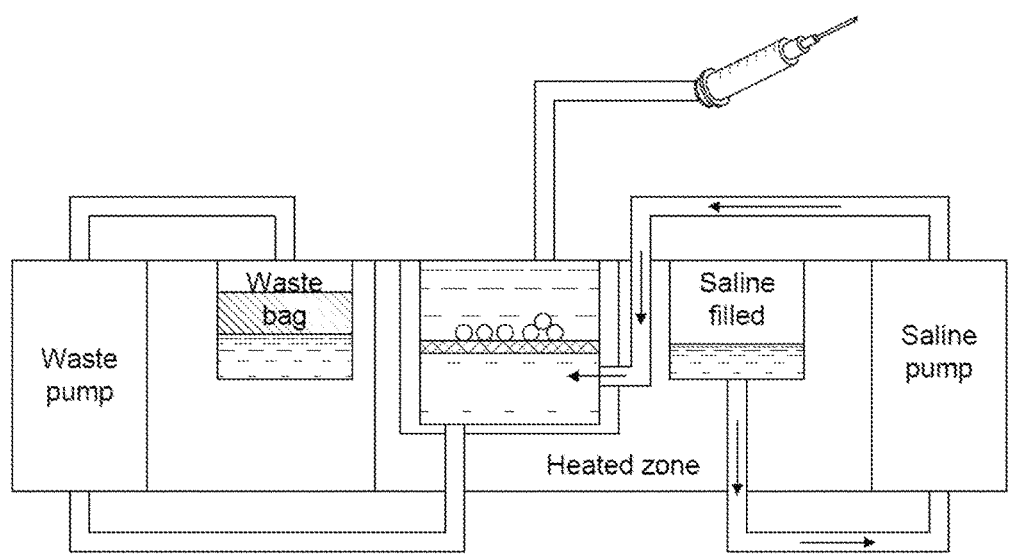
Figure 7G:
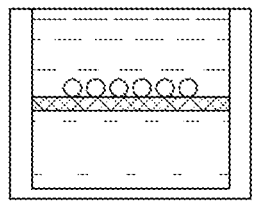

The drop in temperature from the follicle to the culture dish is 2° C.-3° C. This is partly due to significant evaporation related cooling (FIG. 6). It is well known that temperature is important for maintaining the ability of an egg to subsequently divide, i.e. for egg viability and to be fertilised.

Secondly, as the collection vesicle is a test tube, the follicular fluid sits in the test tube which is topped with air. When one test tube is full, the bung is removed, thus exposing the follicular fluid to air, and introducing a risk for contamination, exposure to volatile organic compounds and fluctuations in pH as the $CO_2$ equilibrates to atmospheric air.

Thirdly, identification of the egg by the embryologist is often hindered by the presence of blood cells, and blood clots in the follicular fluid. This can increase the time that eggs are exposed to ambient surroundings. It may also trap the egg in blood clot so that it cannot be identified.

Finally, the current procedure places constraints on the physical proximity and distance in time of the clinician and the embryologist's work. The tasks carried out by the clinician and embryologist are independent and sequential. A woman is brought into theatre, her identity checked with the embryologist and the procedure carried out. The embryologist will take a variable time to process the follicular fluid collected and this usually takes longer than the operative procedure. To ensure that there is no misidentification of eggs, the next woman cannot be brought into theatre until all the preceding woman's follicular fluid has been checked and eggs placed in the incubator. Thus there is currently a time delay between patients, since despite operating time being <10 minutes, the delay between patients is 30 mins, thus compromising staff efficiency.

The follicular fluid must be immediately transferred to the laboratory, requiring close physical links between facilities, restricting facility design and flexibility. To reduce the risks to egg viability described above, the embryologist must be available to isolate the eggs immediately following the procedure to retrieve the eggs, and the embryologist's lab is often situated adjacent or adjoining the clinic.

It is advantageous for there to be a system that would allow collected eggs to be stored for up to several hours following collection without compromise, such that the embryologist's work can be performed independently of the clinic schedule.

The IVF field is regulated by a body, whose Code of Practice requires clinics to have an effective witnessing system to identify and trace the movement of gametes and embryos during clinical/laboratory processes and to prevent mismatch. Despite electronic witnessing becoming routine in several fertility centres it is rarely used in theatre due to having to use several test-tubes per patient. The egg chamber allows one dish to be labelled per patient and thus makes electronic witnessing more feasible in theatre, thus reducing the risk of misidentification of samples.

In some settings it is advantageous to be able to physically separate the locations at which the clinical part of the work, and the embryologist's part of the work are carried out. An example would be if a more complex anaesthetic procedure is required for the woman that would need to be in an theatre that is at a distance from the embryology laboratory. It is routinely done in the practice of 'transport IVF'. In these circumstances the eggs may remain in the test tubes for more than an hour. A system that permits storage of eggs in an environment that does not compromise development potential would be advantageous.

The present invention aims to obviate or mitigate one or more of the limitations or problems associated with the prior art.

According to the present invention there is provided an egg chamber comprising; a vessel which can be made airtight, comprising at least one side wall, an upper wall and a lower wall, at least a portion of the upper wall being transparent and at least a portion of the lower wall being light permeable; a first inlet which can be sealed; a first outlet which can be sealed; a filter with a pore size appropriate for egg collection disposed within the vessel between the first inlet and the first outlet and configured to separate the vessel into a first internal chamber and a second internal chamber.

The inlet and outlet can be provided as sealable ports.

The inlet and outlet may be sealable at sealable ports, or may be sealed upstream or downstream of the chamber for example by the sealing of attached tubing. Sealing of tubing may be for example by heat sealing tubing which is attached to the inlet or outlet.

In a preferred embodiment the sealable ports are self-sealing.

In an alternative embodiment the vessel is made airtight by occluding the tubes attached to the vessel. Occlusion can be achieved by inserting a bung, or by mechanically pinching the tubing (e.g. using pipe clips) or by heat sealing the tubing as indicated above.

Advantageously, as the egg chamber on its own is a single closed unit, this allows the chamber to be advance filled with fluid e.g. buffered medium or saline and the egg collection process to be carried out in a sealed environment. This minimises changes to physiological conditions which may affect the viability of an ovum. In particular, the eggs remain in an enclosed fluid environment at all times. This ensures stability of gas concentrations particularly $CO_2$ and $O_2$ thus enabling a stable pH to be maintained. The enclosed fluid also minimises the risk of contamination and/or exposure to volatile organic compounds (VOCs). This also allows the egg collection process to be continuous between follicles and each ovary, removing the need to utilise multiple collection chambers per procedure. If appropriate all the follicular fluid can be replaced with a buffered medium or appropriate alternative. The eggs may be visible to the embryologist under the microscope through the chamber for initial identification before the chamber is opened and the eggs transferred to the culture medium. The enclosed system also enables the eggs to remain at physiological conditions whilst training staff in egg collection procedures.

Optionally the egg chamber is provided with detachable tubing attached to one or more of the sealable ports.

Optionally the detachable tubing connecting the needle and the chamber, and the reservoir and the chamber are insulated to minimize heat loss.

If the tubes are attached to one or more of the sealable ports, the ports will be open to allow ingress and outflow from the egg chamber. Once the tubes are removed the ports preferably close or are closed to maintain a sealed airtight chamber.

Preferably the filter is planar.

Preferably the filter is disposed between the upper wall and the lower wall.

Preferably the filter extends perpendicular to the lower wall.

Optionally the filter extends at an angle between 25° and 90° from the lower wall. Alternatively, the filter extends at an angle between 45° and 90° from the lower wall.

Preferably the filter extends at an angle of 80° from the wall.

By providing a planar filter extending between the upper and lower walls in this manner, this ensures that when the eggs are collected, the egg chamber can be held in a "collection orientation" where the filter is on a substantially horizontal plane and the upper and lower walls are held in a substantially vertical plane. This allows gravity to assist in drawing blood and other fluid debris through the filter into the second chamber whilst retaining egg in the first chamber. The chamber can then be rotated by an angle of substantially 90° to the "inspection orientation" where the filter is now on a substantially vertical plane and the upper and lower walls being in substantially horizontal planes, essentially forming a sealed lidded pot. In this "inspection orientation" gravity will again act on the eggs such that they fall away from the filter onto the inner surface of the lower wall.

Preferably the filter has a pore size small enough that human ova cannot pass through.

Preferably the filter has a pore size large enough that blood cells can pass through.

This will include a filter of between 1-18 $cm^2$ with a preferred range of between 4 and 10 cm2. The filter will have a pore size of between 20-100 $\mu m^2$ with a preferred range of between 40 and 80 $\mu m^2$, to allow blood cells to pass through but not oocytes. In preferred embodiments the filter will have a pore size between 40 and 60 μm² or less. The filter will be made of a non toxic material, preferably nylon and will be tested using a sperm toxicity test and/or an embryo assay.

In one embodiment the filter is at an angle to the base (viewing mode). In this embodiment the filter may have a lip at the upper end to discourage eggs from sticking.

In one a embodiment the filter is planar. The planar filter encourages eggs to move to the base (in the viewing mode). The planar filter also discourages eggs and blood clots from gathering at the lowest point of the angled filter.

The filter may have a lip at the upper end to discourage the eggs from sticking.

Preferably the lower wall is substantially planar.
Preferably the upper wall is substantially planar.
Optionally the lower wall is entirely translucent.
Optionally the lower wall is entirely transparent.
Preferably the upper wall is entirely transparent.

Advantageously a transparent upper wall and translucent or transparent lower wall means that the egg chamber can be used as a sealed unit on a microscope and an embryologist does not need open the vessel and alter the physiological balance therein to examine the contents.

Preferably the first inlet is positioned on a side wall associated with the first internal chamber.

Alternatively the first inlet could be positioned on the upper wall (or lid) associated with the first internal chamber.

Preferably the first inlet is positioned such that it is uppermost on the egg chamber when said chamber is in the "collection orientation".

Preferably the first outlet is positioned on a side wall associated with the second internal chamber.

Preferably the first outlet is positioned such that it is lowermost on the egg chamber when said chamber is in the "collection orientation".

Preferably, the side walls may run parallel in a direction from the first internal chamber to the second internal chamber. Alternatively, the side walls may taper together in the direction from the first internal chamber to the second internal chamber.

Preferably where the lower wall meets the side wall in the first internal chamber, there is an incline.

Optionally the incline is a radial incline.

Optionally the egg chamber further comprises an air sensor adapted to detect if any air is aspirated into the first internal chamber.

It should be noted that it is also possible to visually detect air in the chamber.

Preferably the egg chamber further comprises an air outlet port.

Preferably the air outlet port is positioned such that it is located towards the uppermost portion of the egg chamber when said chamber is in the "collection orientation".

It is possible that air may be aspirated into the first internal chamber during egg collection. Advantageously this should be visible during the collection procedure in the 'collection orientation'. Advantageously this can be detected using an air sensor or can be determined visually. Collected air can be removed via the air outlet port.

Optionally the lower wall of the upper chamber may be provided with visual markings. Preferably the visual markings are a grid.

The advantage of providing a visual marker on the lower wall is that, as the eggs lie on the lower wall during inspection; this can make it easier and quicker for an embryologist to identify the eggs prior to transfer without needing to remove the lid or open the sealed egg chamber. The lower wall will ideally will be of a thickness similar to that of IVF culture vessels (between 0.1 and 3 mm) that will allow the embryologist to transfer oocytes into another culture vessel without having to change the focus of the microscope.

Optionally a flow directing device (or flow restriction device) is positioned in the upper chamber.

A function of this device is to reduce the fluid turbulence as it enters the chamber. This is to reduce physical stress of the eggs and to encourage direct movement of blood cells to the lower chamber. A function of this device is also to reduce the pressure of fluid on the filter. This reduces the risk that the egg may become trapped in the filter. A function of this device is also to reduce the volume of fluid that might be needed to flush all the blood cells from the chamber. A function is to reduce the total fluid volume in the chamber such that, when the upper wall is removed by the embryologist, the surface level of the fluid will be below the level of the side wall (in 'microscope orientation'). A function is to act as a collecting point for droplets of fluid as the lid is lifted so that they fall back into the chamber. A function is to reduce the risk that eggs will be sucked back into the air outlet port.

Preferably the flow directing device is a baffle. This baffle is preferably attached to the upper wall. Most preferably the baffle is integral to the upper wall and protrudes downwards from the lid (lower surface of the upper wall) into the chamber in the viewing configuration. Alternatively it could be attached or integral to the lower wall or the side walls, or any combination. Preferably it is removed with the upper wall when the chamber is opened to remove the eggs.

Preferably the baffle is positioned between the inlet port and the filter.

Optionally the baffle is linear and in the horizontal position in the 'collection orientation'. Preferably it is at 90-95° to the attached part of the chamber.

Alternatively the baffle is not in the horizontal position in the 'collection orientation'.

Preferably, the baffle is "V" shaped such that the bottom of the V is lowest in the collection orientation.

Preferably there is a space of about 1-5 mm between the baffle and the lower wall.

Preferably there is a space of 0.5-3 mm between each end of the linear baffle and the side walls.

Advantageously, the linear baffle may be between 1 mm and 8 mm wide. Preferably the linear baffle may be 5 mm wide.

Preferably it is positioned near the inlet port in the upper part of the chamber in 'collection orientation'.

Alternatively it is positioned in the lower part of the upper chamber in the 'collection orientation'.

The baffle may be curved or angled.

An alternate option to reduce the flow rate as the fluid enters the chamber is a variation (increase) in the diameter of the tubing before it enters the chamber. This could be before or after the inlet port or be integrated into the port opening. A further alternative would be to increase the distance between the inlet and the baffle, however this is somewhat less preferable as it could result in more reagents being required.

The baffle will be made of a non toxic material, preferably polystyrene or glass and ideally will not cause major obstruction of eggs whilst being viewed under the microscope.

The presence of a baffle reduces the volume of fluid required to clear blood cells from the central cavity from >200 ml to less than 60 ml.

Preferably all corners where two internal planes meet will have a radius >0.05 mm and <10 mm. This is to prevent eggs and other follicular fluid gathering in 90 degree corners.

So the operator can retrieve an egg, the vessel needs a lid or access point that can be removed.

One option is to have a screw thread type lid which can be removed.

Another option is to have a friction push fit lid

Another option is to have a location fitting lid which is mechanically pushed onto a gasket and held in place, compressing the gasket to make a seal.

Another option is to have a heat sealable lid. This may be combined with the screw thread lid or the friction push fit lid.

Rounded edges at connecting points of lid and chamber ensure eggs are not trapped in the shadow of connecting points (i.e. right angles tend to be a problem).

Advantageously, the lid may have a thickness between 2 mm and 10 mm.

The lid may have a lip to cover the top 5-25% of the filter to avoid eggs getting trapped in this area of the filter.

Preferably the vessel will have visual or mechanical means of seeing if a unit has been tampered with, used or opened.

Optionally this would be an adhesive tag that bridges between the parts of the unit that can be separated. The tag would tear on beginning removal of the lid.

Optionally it could be a tag that is heat pressed onto the chamber.

Alternatively it can be a frangible section that bridges between the parts of the unit that can be separated.

Optionally a unique tool for opening the lid may be provided. The unique tool enables the lid to be removed with lowest risk of spillage.

Preferably any optional ports required to remove trapped air from the vessel will include a filter with a pore size of between 20-100 μm. This is to allow air and blood cells to pass out of the chamber but not ova.

Advantageously, a filter covers the outlet port on the inner side of the chamber.

Preferably the filter will be on the inner most face where the port opening meets the chamber wall. Optionally the filter could be set back in line of the filter outlet. Advantageously, the vessels may be stackable for ease of storage.

According to a second aspect of the present invention there is provided an egg collection system comprising the egg chamber of the first aspect and a pump station; said egg chamber connected via the first inlet port to a first tube and needle and further connected to a second tube via the outlet port; said pump station comprising a first priming pump associated with a sterile liquid reservoir and the first tube and a second aspirating pump associated with the second tube and adapted to draw fluid through from the needle, via the egg chamber to the outlet tube.

Preferably the second tube is associated with a waste reservoir.

Preferably the priming pump is a peristaltic pump.

Most preferably both the priming pump and the aspirating pumps are peristaltic pumps.

Optionally the aspirating pump could be a vacuum pump.

Preferably the egg chamber is received within a heated housing.

Most preferably at least part of the heated housing allows the egg chamber to be viewed.

Most preferably the heated housing is adapted to hold the egg chamber in the "collection orientation".

According to a third aspect of the present invention there is provided a method of collecting eggs or ova from an animal, using the egg collection chamber of the first aspect comprising the steps of;

obtaining the egg chamber with a first tube connected to the egg chamber via the first inlet port, the first tube being associated with a needle, and a second tube connected via the outlet port;

priming the egg chamber by filling the egg chamber, first tube, second tube and needle with a liquid;

aspirating follicular fluid through the needle into the egg chamber, such that the fluid is drawn through the filter disposed within the egg chamber thus retaining eggs in the first internal chamber of the egg chamber.

According to a fourth aspect of the present invention, there is provided a fluid pump system for IVF egg collection, comprising:

a first fluid pump having a first inlet port and a first outlet port, said first inlet port is operatively coupled to a first reservoir via a first fluid connection, said first outlet port is operatively coupled to an extraction port via a second fluid connection and to a second reservoir via a third fluid connection, wherein said extraction port and said second reservoir are connected via a fourth fluid connection;

a second fluid pump having a second inlet port and a second outlet port, said second outlet port is operatively coupled to a third reservoir via a fifth fluid connection, and said second inlet port is operatively coupled to said second reservoir via a sixth fluid connection;

a plurality of selector valves adapted to establish selective fluid communication between any one of said first fluid pump, said extraction port, said first reservoir, said second reservoir, said third reservoir and said second fluid pump, and a controller adapted to selectively actuate any one of said plurality of selector valves.

This provides the advantage that the fluid pump system can be full primed, i.e. filled with fluid, flushed, vented (air removal), and operated to collect, for example, egg(s) either fully automatically, controlled by a pre-programmed controller, or at least semi-automatically by manually triggering a required operating mode in the controller. Providing a much improved, efficient and highly repetitive egg collection procedure that minimises the risks damaging the collected eggs during extraction.

Preferably, said first fluid pump and said second fluid pump may be peristaltic pumps.

Advantageously, a first selector valve and a second selector valve may be operatively coupled within said second fluid connection, said first selector valve and a third selector valve may be operatively coupled within said third fluid connection, said second selector valve and said third selector valve may be operatively coupled within said fourth fluid connection, and at least a fourth selector valve may be operatively coupled within said sixth fluid connection. Even more advantageously, said second outlet port may be operatively coupled to said second reservoir via a seventh fluid connection, in parallel to said sixth fluid connection.

Preferably, a fifth selector valve may be operatively coupled within said seventh fluid connection.

Advantageously, said controller may be adapted to execute at least one predetermined sequence of actuating any one or any combination of said plurality of selector valves and/or said first pump and/or said second fluid pump.

Optionally, said predetermined sequence may be triggerable through at least one external actuator. Preferably, said at least one actuator may be a foot pedal switch. Preferably, said extraction port may be coupleable to a recovery needle adapted to extract follicular fluid.

Advantageously, the fluid flow rate provided by said first fluid pump and said second fluid pump may be selectively adjustable.

Preferably, said controller may further comprise a user interface adapted for inputting commands to the controller. Even more preferably, said user interface may be further adapted to display the operating mode of said fluid pump system and/or at least one predetermined physical property within said fluid pump system.

Advantageously, any one or all of said first, second and third reservoir comprise may be operatively coupled to an adjustable heat source controllable by said controller.

Preferably, any one of said first to seventh fluid connection may be formed from flexible tubing.

Advantageously, any one of said plurality of selector valves may be a pinch valve adapted to be actuated by said controller.

Preferably, said second reservoir may be an egg chamber according to the first aspect of the present invention.

Figure 2A:
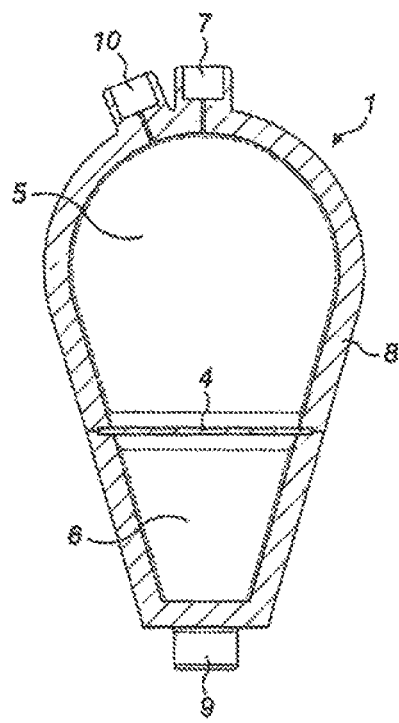
Figure 2B:
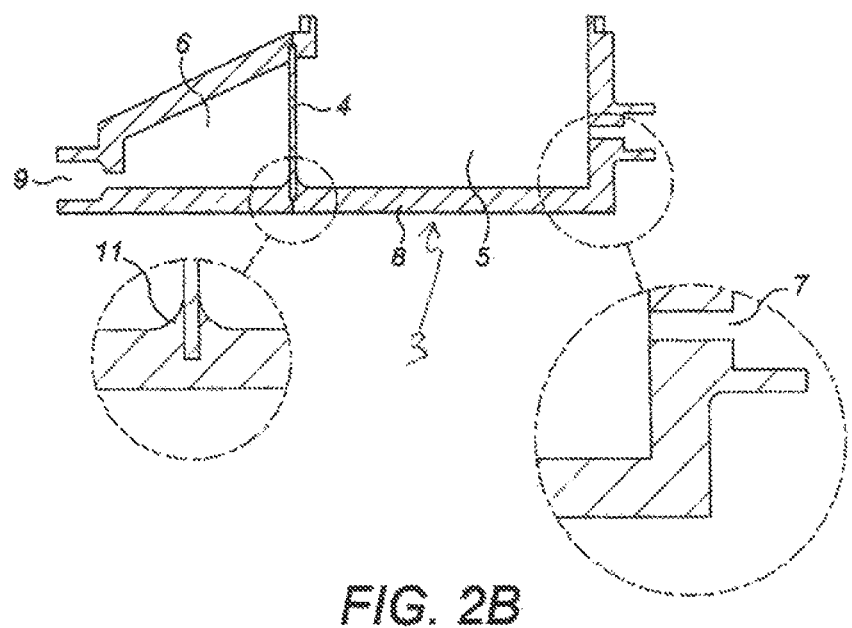
Figure 4:
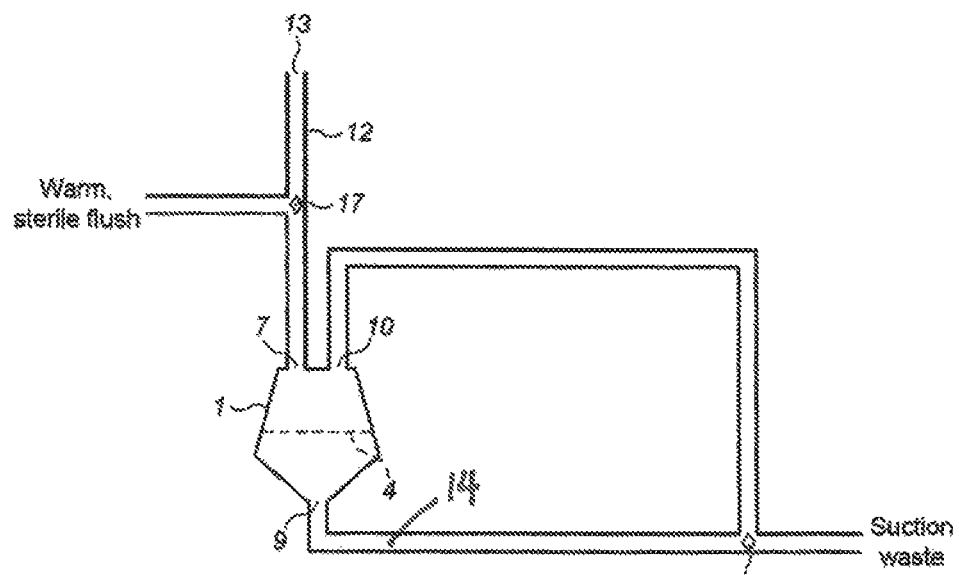
Figure 8:
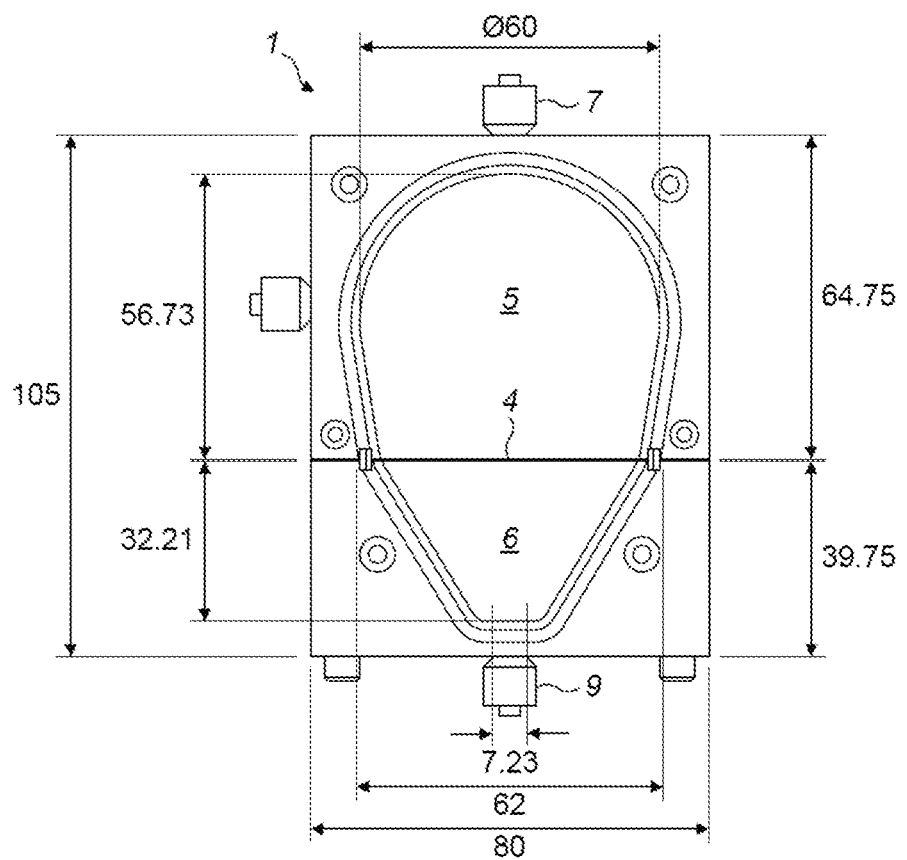
Figure 9:
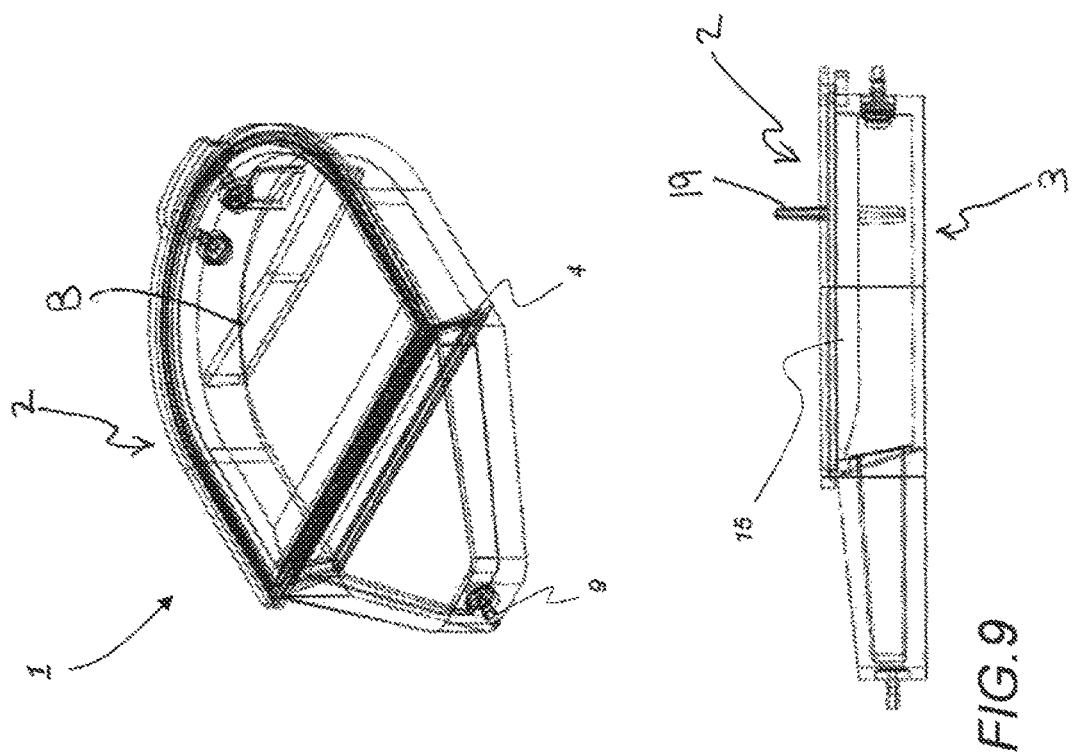
Figure 9:
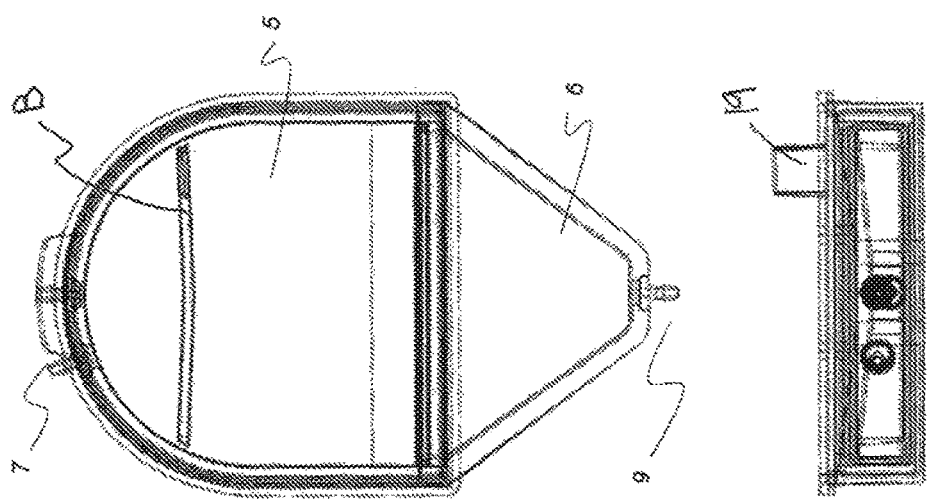
Figure 10:
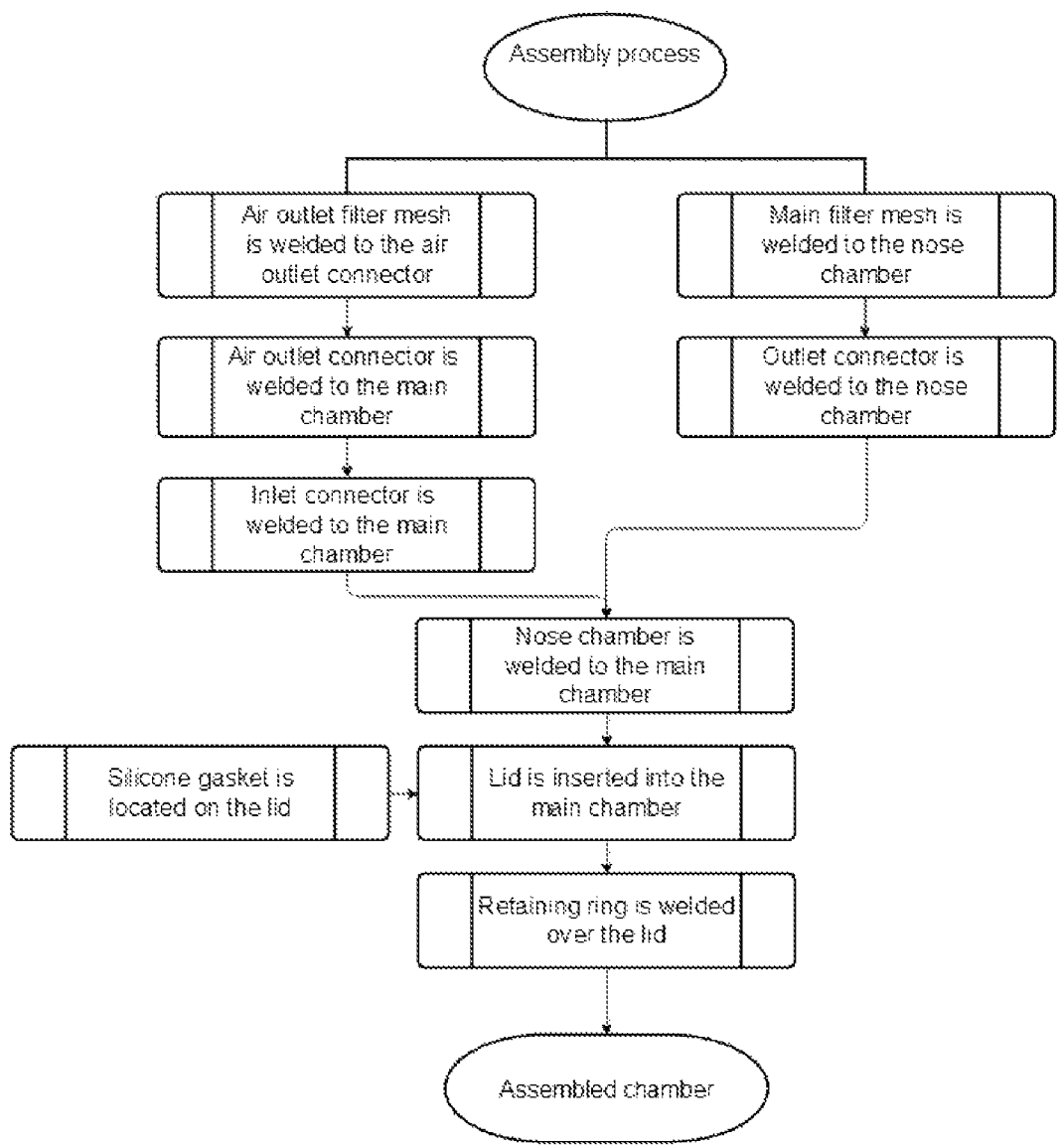
Figure 11:
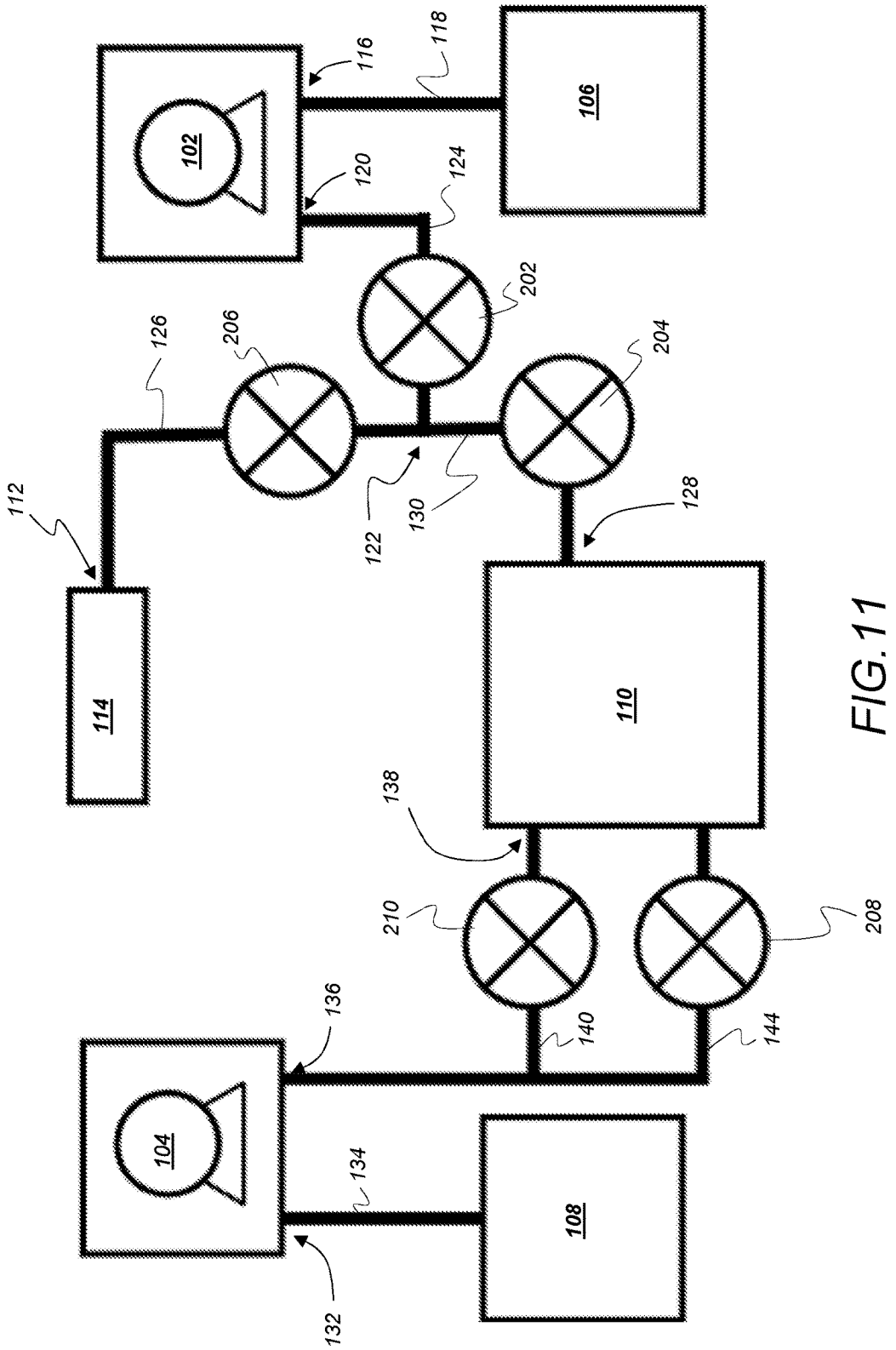
Figure 12A:
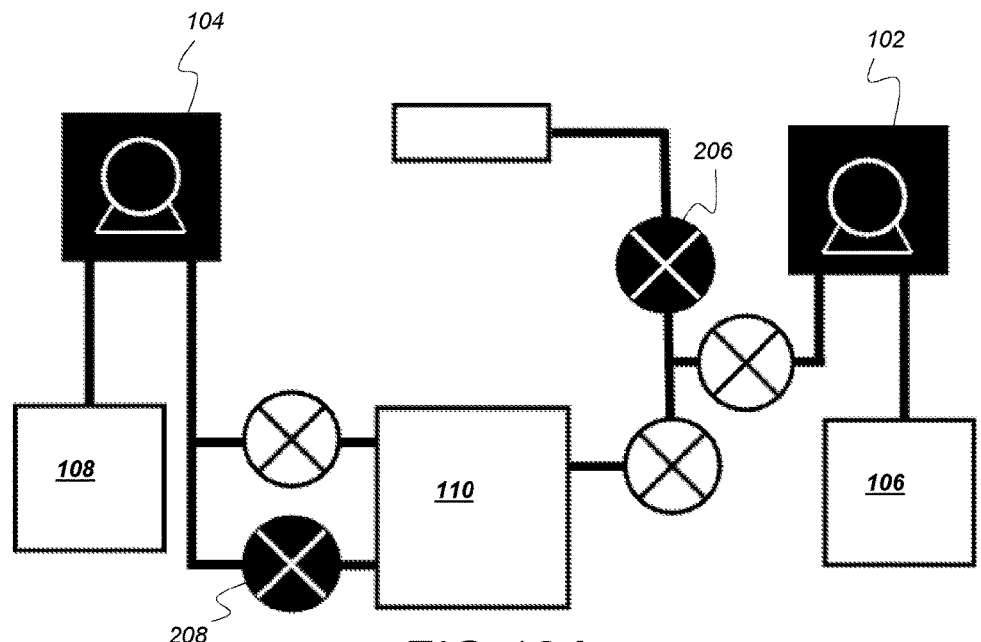

In order to provide a better understanding of the present invention, non-limiting embodiments will now be described with reference to the following figures in which:

FIG. 1A is a perspective view of an egg chamber according to the present invention; and FIG. 2A shows section views of the change of the egg chamber in the collection orientation (A), and the inspection orientation (B); and FIG. 2B shows section views of another embodiment of the egg chamber in the collection orientation (A), and the inspection orientation (B); and FIG. 3 shows a diagram of the prior art system which uses a test tube and bung; and FIG. 4 shows a schematic diagram showing the priming system/flushing system; and FIG. 5 is a diagram showing the effect of changes in temperature during oocyte collection. Media was aspirated into either the conventional oocyte collection chamber (Conventional) or into the prototype of CHUMP1 (CHUMP1). The temperature was recorded at 1 minute intervals. The loss of temperature was greater using the conventional system as was the time to recovery (n=7; $P<0.001$). This is believed to results from increased evaporation using the conventional system; and FIG. 6 demonstrates the cooling that occurs during standard oocyte collection procedures and the potential benefit of a closed system. The inventors carried out 6 mocked oocyte aspirations using medium at physiological starting temperature using the conventional system. The temperature of the aspirated medium was measured in the open test tube over a period of 5 minutes. A significant cooling was seen (blue line) in (A). The inventors then overlaid the medium with oil and showed that this cooling did not occur. This confirmed that the cooling resulted from evaporation; and FIG. 7 A-G is a system diagram showing the egg collection system in use. (A) Step 1: Load collection vessel into heated block. A saline and waste bag need to be routed through two peri-pumps and then attached to the collection vessel via luer locks. The oocyte recovery needle is attached. (B) Step 2: The saline pump is activated via a foot switch filling the collection vessel with warm saline solution. Continuing to pump fluid once the vessel is full will prime the recovery needle too. (C) Step 3: Once the needle is positioned in the correct location the waste pump can be activated. This provides the suction to harvest the embryos. (D) Step 4: Unwanted debris in the follicular fluid is removed from the collection vessel sample via the waste pump. (E) Step 5: Once collection is complete any follicular fluid remaining in the recovery needle is drawn through the lines ensuring all embryos are in the collection vessel. (F) Step 6: Enough warm saline solution is pumped into the vessel to expel any trapped air. (G) Step 7: The segment of the heated area that contains the collection vessel can be removed for transport to a nearby heating station. This would not be 'powered' but would contain enough latent heat to transport the collection vessel around a room or to an incubator; and FIG. 8 is a plan view of a first design of an egg chamber according to the present invention; and FIG. 9 is a second, preferred, design of an egg chamber according to the present invention; and FIG. 10 is a flow diagram showing the chamber assembly process; and FIG. 11 is a simplified schematic of the fluid pump system according to the third embodiment of the present invention; and FIG. 12 A-D is a illustration of the system (A) during the "Fill Chamber" sequence, (B) during the "Flush" sequence, (C) during the "Remove Air" sequence and (D) during the "Collect Eggs" sequence, wherein blacked-out system components indicate active system components; and FIG. 13 illustrates a simplified high-level main process flow chart as executed by the controller; and FIG. 14A-E is an illustrative example of (A) the controller user interface, and the controller user interface during different sequences: (B) "Collecting Eggs", (C) "Flush", (D) "High Pressure" and (E) "Collecting Eggs at High Pressure"; and FIG. 15 is an illustratrative example design of the fluid pump system viewed (a) from the top, (b) perspective view, (c) from the side and (d) from the front.

An egg chamber 1 is generally depicted in FIG. 1. The egg chamber 1 is in the form of a closed vessel with a substantially planar upper wall 2 and a substantially planar lower wall 3. The vessel also has an appropriate number of side walls 8 to form a polyhedron (it would be appreciated that one or more of the walls could be curved rather than planar as in FIG. 1. The upper section of the chamber including the upper wall 2 is separable or detachable from the lower section of the chamber 1, however in normal use during egg collection and review, the upper section and lower sections of the egg chamber 1 are combined with a liquid tight and substantially airtight seal.

The egg chamber 1 can be formed for example by injection moulding, rotational moulding, extrusion, vacuum forming, compression moulding, or by three dimensional printing.

In one embodiment the chamber 1 is made out of a thermosoftening of thermosetting material. Examples of thermosoftening plastics include acrylonitrile butadiene styrene, polyamide (Nylon), acetate (or cellulose), acrylic, polymethylmethacrylate, polypropylene, polystyrene, low density or high density polyethene, polyvinyl chloride, polychloroethene, uPVC. Examples of thermosetting plastics include, polyester resin, epoxy resins, and polycarbonate. In a preferred embodiment the chamber is made out of polystyrene, however in another embodiment the chamber is made out of glass, preferably purified glass.

The chamber 1 may be coated with a substance such as nanocrystalline diamond. In a preferred embodiment, at least the inner part of the upper chamber is coated.

The egg chamber 1 contains a filter 4 that separates the vessel into a first chamber 5 (the egg collection chamber) and a second chamber 6. The filter 4 extends between the upper wall 2 and the lower wall 3 effectively bisecting the vessel. In this embodiment the filter 4 is planar and extends substantially perpendicularly from the lower wall 3. In an alternative embodiment the filter could be curved, however this is less preferable as blood clots and eggs could collect in the same place making eggs more difficult to identify in blood clots. The filter 4 may be at an alternative angle, for example at an angle greater than 25° from the lower wall 3, ideally, at an angle between 25° and 90° from the lower wall 3, and preferably 70°. Optionally, the angle may be between 45° and 90°. The pore size of the filter is selected to allow blood and other debris to pass through but not to allow an ovum to pass through. In one embodiment the filter has a pore size of 60 to 64 microns. As blood cells are 8-10 microns the filter could be greater than 10 microns but small enough to retain an ovum. It is preferred that the pore size be lower than that which would be used for, for example, an embryo collection device.

The first chamber 5 has an inlet port 7 positioned on the side wall. It is preferred that the inlet is positioned such that when the egg chamber 1 is oriented for collection such that the first chamber is above the second chamber and the filter 4 is substantially horizontal, the inlet is at the highest point. It can be seen that, when in this orientation, the side walls associated with the second chamber 6 taper towards each other to encourage fluid to flow towards an outlet port 9 which is positioned on the side wall of the second chamber 6. When oriented for collection the side walls are shaped to form a funnel.

Preferably the outlet port will be at the lowest position in the 'collection orientation' to allow gravity to assist the removal of all blood cells into the outlet tube. Alternatively the port could be either at a different position on the side wall or be on the upper wall.

Preferably the size of the second chamber should be small to reduce the volume of fluid needed to flush the chamber to be clear of blood cells.

A flow directing device is positioned in the first chamber. In the preferred embodiment this device is in the form of a baffle B (FIG. 9), which may be linear or curved, which acts to reduce the fluid turbulence as it enters the chamber. This is to reduce physical stress of the eggs and to encourage direct movement of blood cells to the lower chamber. In another embodiment the fluid directing device is attached to the base of the chamber (in viewing mode). There may also be a mechanism to reduce fluid level upon removal of lid to reduce the risk of fluid spillage. This could be achieved, e.g. by incorporating the fluid directing device into the lid, such that the baffle is removed from the chamber along with the lid, thus reducing the fluid level.

Where the lower wall 3 meets the filter 4 the surface is tapered slightly to provide a smooth incline 11 (FIG. 2B). This encourages any eggs to lie away from the filter 4 when the egg chamber 1 is positioned in the viewing orientation. This makes any eggs that are collected easier to see and less likely to be hidden in shadowed corners of the first chamber.

Both the inlet port 7 and the outlet port 9 may be self sealing ports. When the ports are closed the egg chamber 1 is a closed, fluid tight and airtight vessel. The ports are suitable for use within an isolator or a class 2 hood.

In one embodiment the self-sealing ports are luer-type or twist-to-connect couplings.

It is desirable that the ports are medical grade and allow for a one hand disconnect. Most preferably the ports can be provided with an audible disconnect (click) which will alert the user that the disconnect has occurred. The ports should be leak free, non-spill valves which include mechanisms to prevent accidental disconnect. Ports should allow rotation of the connected tubes as this prevents kinking. It is also preferred that the ports have elastomeric seals. The ports and other elements of the chamber should be gamma ray sterilizable.

Ideally the ports should allow for a gap-free flow path that provides better flow and eliminates stagnant flow areas.

Examples of appropriate self sealing ports include SMC Polycarbonate series couplings (Colder Products Company), which are a twist-to-connect coupling that provides a reliable and more secure alternative to luer-type connections. They also allow for the tubing to rotate freely when connected. Another example is the SRC small bore connector (Colder Products Company), which eliminates the potential for misconnection with luer fittings. NS4 ABS Series couplings (Colder Products Company) feature non-spill valves in a compact size and medical-grade material.

Alternatively, rather than self sealing ports, a tube sealing machine, such as CompoSeal® Universal (Fresenius Kabi) could be used to seal tubes which are associated with the inlets and outlets of the chamber to provide an airtight chamber. In the shown embodiment, an air outlet port 10 is also associated with the first chamber. Again, this is included on the side wall and allows any air that may enter the system during use to be removed easily. There may also be a sensor in first chamber which shuts off system when air is detected and prevents more air entering the system.

The upper wall 2 of the vessel is transparent to allow visual inspection of the contents of the vessel without opening. In the embodiment shown, substantially the entire upper wall is transparent, which is preferred as it allows both the first chamber 5 and the second chamber 6 to be viewed. It would be understood however that an alternative is that only part of the upper wall 2 is transparent, providing that it allowed visual inspection of the first chamber 5 which is the egg collecting chamber.

The lower wall 3 of the vessel is also transparent in the depicted embodiment. This ensures that if the egg chamber 1 is placed on a light microscope for visual inspection of its contents, light will be able to enter through the lower wall 3. Again it will be appreciated that an alternative is that only part of the lower wall 3 is transparent, providing that it allowed visual inspection of the first chamber 5 which is the egg collecting chamber.

Where the chamber 1 comprises transparent and/or translucent material the material is preferably non-pyrogenic and non-toxic. Most preferably the material passes endotoxin, sperm toxicity and embryotoxicity tests. Preferably the material achieves results of <0.25 EU/ml, preferably <0.03 EU/ml in in vitro bacterial endotoxin tests. Example tests include gel-clot, kinetic turbidimetric and chromogenic methods (quantitative). The material would also preferably pass a sperm toxicity assay, such as the sperm motility assay (http://www.ncbi.nlm.nih.gov/pubmed/10875871), and/or stem cell assays for toxicity. The material also preferably passes an embryotoxicity assay. Example assays include Embryonic Stem cell Test (EST), the Zebrafish Embryotoxicity Test (ZET) and the rat postimplantation Whole Embryo Culture (WEC). Preferably the result of such an assay would be >80% expanded blastocytes by 96 hours.

The chamber 1 should meet the requirement of USP Class VI testing and can be sterilized according to the standards required for medical devices.

In an embodiment not shown but envisaged by the inventors the lower wall could be provided with grid markings or other visible indices that will assist with viewing and locating eggs within the first chamber.

The dimensions of the egg chamber 1 are chosen to be similar to equipment already used by clinicians and embryologists e.g. similar dimensions to a typical petrie dish or collection vessel currently used by an embryologist. The dimensions are also selected to allow the egg chamber 1 to be suitable for viewing under a microscope.

The egg chamber will be between 2-16 cm$^2$, preferably 4-10 cm$^2$.

The chamber will be made of a non toxic plastic such as polystyrene or glass.

The egg chamber 1 is preferably integratable with an automated collection system comprising a pump. The system is shown in FIG. 7. The egg chamber 1 is configured to attach to tubing which attaches the chamber 1 via ports to an egg collection needle, a flushing fluid reservoir and a waste collection unit. The egg chamber is configured to fit within a temperature control system. In one embodiment the temperature control system comprises a heated block, which is configured to receive the egg chamber in only one orientation. In another embodiment the tubing and the pump is housed within a housing system which is temperature controlled. The automated collection system comprises a mechanism to connect the tubes to the pump in the correct configuration, such as numbered or colour-coded clips, or tubing of differing lengths. Such a mechanism reduces or prevents operator error when connecting the device to the automated collection system.

The egg chamber 1 is used as follows;

An egg chamber 1 is provided with tubing 12 attached to the inlet port 7. The distal end of the tubing 12 (i.e. the end further from the vessel) is attached to a collection needle 13. The egg chamber is also provided with a second tube 14 attached to the outlet port (FIG. 4). This second tube 14 is associated with a waste reservoir at its distal end. The second tube 14 is also associated with a suction pump adapted to draw fluid through the tube from the egg chamber 1 to the waste reservoir. This pump may be actuated by a foot pedal. In all cases the tubing is kept as short as practicable.

The egg chamber 1, along with the tubing 12 and needle 13 are all primed by being filled with warmed sterile liquid e.g. saline solution. The tubing 12 between the needle and the inlet port 7 is provided with a three way tap 17 (shown in FIG. 4) such that the tubing 12 can also connect to a warm sterile liquid reservoir 18 as well as the needle 13 and the inlet port 7 of the egg chamber 1. Pinch valves can be used to open or close the fluid flow options as required. A peristaltic pump can be actuated to push sterile liquid from the sterile liquid reservoir through the tubing 12 into both the egg chamber 1 and the needle 13.

The egg chamber 1 is completely filled with fluid. It is also preferable that the egg chamber 1 is held on a heated plate, or within heated housing, to maintain the chamber 1 at or close to body temperature. The heated plate or housing can be associated with the pumps used to draw liquid through the system as part of a larger pumping unit. It is preferable that the fluid is heated to 36.8±0.4° C. 37° C.

During egg collection, the egg chamber is held in the "collection orientation" where the filter 4 is substantially horizontal within the chamber. This promotes the effect of gravity when aspirating the follicular fluid and attempting to separate eggs or ova from any blood or debris within the chamber 1.

Egg collection is usually a day procedure with the patient under sedation. The needle 13 is passed through the top of a patient's vagina under ultrasound guidance into the ovary. Follicular fluid, and associated ova, is aspirated by drawing fluid through the system. An aspirating pump is used to draw the priming liquid out through system into the waste reservoir, which pulls the follicular fluid, including any ova, through the needle 13 and tubing 12 into egg chamber 1 through the inlet port 7. The fluid is drawn into the vessel through the inlet port and into the first chamber 5, and then further drawn through the filter 4 into the second chamber 6. The baffle slows the flow of fluid which spreads out across the length of the baffle. It then flows over the baffle as a 'curtain' flow at a reduced speed. The eggs and blood cells pass over the baffle and fall towards the filter. As the pore size of the filter 4 of between 10-100 µm, preferably between 20-60 µm is selected to be smaller than that of an ovum/egg the eggs are retained in the first chamber 5 whilst the follicular fluid, blood cells and other smaller sized debris passes through the filter 4 into the second chamber 6 and ultimately is drawn out of the outlet port 9 into the waste reservoir. The pore size enables this separation to occur mainly by gravity thus requiring minimal aspiration pressure across the filter. This results in the eggs being retained in the first chamber 5 in a clear fluid environment. It is important that the eggs are separated in this way from blood present in the follicular fluid to prevent blood clots from forming.

Notably, as all of the eggs are collected in a single vessel, with follicular fluid being drawn through the system ultimately into the waste reservoir, this reduced the amount of fluid that an embryologist must search through to identify and select appropriate ova/eggs.

The sealed chamber is kept in an incubator until the embryologist is ready to inspect and open it.

It is possible that an egg may be positioned within the tubing 12 after aspiration if it has not yet been drawn through the inlet port 7. At the end of the collection the clinician is able to use the priming pump to ensure all follicular fluid has been pushed into the egg chamber 1 and no eggs or ova are inadvertently left in the tubing 12.

If there is concern that eggs may have been retained in the needle after being withdrawn from the woman, the needle can be inserted into sterile warm fluid e.g. saline, and flushed.

In an embodiment not shown, the egg chamber is also provided with an air sensor which detects whether air is entering the first chamber during aspiration. There is a risk that air can enter the system during aspiration of the follicle which can affect the pH of the follicular fluid or liquid in which the eggs or ova are held or, in more significant cases can result in the egg drying out. The sensor would be positioned at the top of the first chamber when the chamber is oriented for collection. The air outlet port 10 could then be opened to remove any air to minimise the changes to the physiological conditions surrounding the collected egg (e.g. changes to the pH) and to prevent the egg from drying out. The air outlet port 10 can also be used without a sensor being present.

It is also possible to flush out the needle if it becomes blocked during the collection process. The tubing 12 between the needle and the inlet port 7 can be provided with a three way tap 17 (shown in FIG. 4). The flow between the needle and inlet port 7 can be closed at point A, for example using a pinch valve, and a flow between a sterile liquid reservoir and the needle can be opened, for example at point B. A pump, preferably a peristaltic pump, is used to push the sterile liquid from the sterile liquid reservoir out through the needle, dislodging anything that may be blocking the bore of the needle or associate tubing. Once the flushing is complete, the flow between the sterile liquid reservoir and the needle can again be closed and the flow between the need and the inlet port 10 can be reopened. During flushing the aspirating pump associated with aspiration will usually be stopped.

The egg chamber 1 can then be detached and disconnected from the tubing 12 associated with needle 13 and also from second tube 14. As the ports 7, 9, 10 are sealable (preferably self-sealing) and non-drip this results in the chamber being a sealed environment for the collected eggs. Throughout the collection process the egg chamber 1 is kept on a hot block to ensure that the egg chamber 1 and its contents are all held at body temperature, 37° C., or at the temperature desired by the embryologist (in some cases embryologists prefer to hold the eggs at a temperature slightly higher or lower than body temperature). The chamber can be retained at a constant temperature such as body temperature and the ova/eggs can be held in the chamber for some time if required.

Once the eggs are collected the next stage is for an embryologist to inspect and select the most viable eggs/ova for further use in the procedure. As best shown in FIG. 2, the egg chamber 1 is moved/re-oriented by an approximately 90° angle from the "collection orientation" where the filter 4 is in a substantially horizontal plane within the chamber, to the "inspection orientation" where the lower wall 3 is now the lower surface and the filter 4 is on a substantially vertical plane. This change in orientation allows the embryologist to place the still sealed egg chamber 1 onto a microscope, the egg chamber now being in the inspection orientation, for viewing. Advantageously this orientation also allows for easy storage and transit of the egg chamber 1. The lower wall 3 is transparent and allows light to enter the chamber which is particularly useful when a microscope with a lower positioned light source is used (i.e. a light source is positioned below the egg chamber 1). Any eggs/ova that are present are held in the first chamber 5 and, as the egg chamber 1 is in the viewing orientation, they will be resting on the floor of the chamber which is now the inner surface of the lower wall 3. The eggs/ova are encouraged away from the edges of the first chamber, particularly away from the filter which is where they would most likely have been located when the egg chamber 1 was in the collection orientation, by providing an inclined surface 11 or radius edges where the lower wall 3 meets the filter 4 and/or where the lower wall 3 meets the one or more side walls 8. As the upper wall 2 is also transparent the embryologist can view the content of the egg chamber 1 without having to open it or unseal the unit. The orientation of the chamber also ensures that the filter does not obscure the embryologist's view. The lower wall can be provided with marking or indices, e.g. a grid pattern, to assist the embryologist in locating eggs or ova. Up to this point the eggs/ova will have been retained in an essentially sealed fluid (and more preferably liquid) environment with minimal or no changes in temperature or pH and minimal or no ingress of air.

It will be appreciated that although the entire upper wall is transparent in this embodiment an alternative embodiment could have only a window portion of the upper wall being transparent providing is was of a sufficient size to allow the embryologist to view the content of the first chamber. There is some benefit to also being able to visualise the content of the second chamber as, during collection, the practitioner will often wish to see whether significant amount of blood is being pulled through from the follicle. Any remaining walls or sections of the vessel may optionally also be transparent or translucent to allow viewing of aspirated fluid from any angle.

Once the embryologist has inspected the eggs and identified those which appear most viable they can then remove the lid portion 15 (FIG. 1) of the egg chamber 1, the lid portion 15 comprising at least a portion of the upper wall 2, and in the embodiment depicted in FIG. 1, all of the upper wall 2. The lid portion may be provided with a protruding section 19 which can be gripped by the user to facilitate removal of the lid portion 15. Preferably the protruding section 19 is positioned to the side of the lid portion 15 in order to avoid obscuring the view into the chamber. In one embodiment the lid is removed by twisting (rotating) whilst in others the lid portion 15 may simply be lifted away from the base portion 16. Preferably less than 20 degrees rotation is required to remove the lid, more preferably less than 10 degrees. The lid can be circular or non-circular. Up until this point, the lid portion 15 has been sealed with a liquid tight and airtight seal to the base portion 16 of the egg chamber 1. This has ensured that the egg chamber has been entirely air tight and fluid tight post aspiration to prevent physiological and environmental changes such as changes to pH and temperature or ingress of air or oxygen or contact with contaminants. It is preferred that this is a heat seal, tamper proof tape or a silicon seal that once broken cannot be resealed. This would ensure that the egg chamber is single use and tamper proof. In one embodiment the lid 15 is sealed to the base portion 16 using a retaining ring. The retaining ring is preferably single use being adapted to break when the lid 15 is removed from the base 16. The retaining ring may be provided with a tabbed portion which extends out from the chamber to facilitate removal of the retaining ring from the chamber when required. A single use chamber also allows for easier patient tracking as the egg chamber 1 can be provided with a patient identifier. The patient identifier may be a permanent identifier. With the lid portion 15 removed the embryologist can remove the selected eggs using a pipette using known techniques. The collected eggs or ova can then be used further.

One embodiment of a lid is a compression fit lid. Here a tool is provided to remove the lid. In one embodiment the tool is a key which when inserted into the lid and rotated, enables the lid to be removed. In one embodiment the receiving area for the tool (keyhole) is located in the area of the lid incorporating the flow direction device.

Referring to FIGS. 8 and 9, two slightly different designs of the egg chamber are disclosed. In FIG. 9, which discloses the preferred design, the sides of the upper chamber 5 are straight and not tapered as in the design shown in FIG. 8. Also, the baffle B forms a V shape (FIG. 9) and is attached to the underside of the lid 15 and the shape of the lid 15 matches the shape of the upper chamber 5 (i.e. flat bottom, parallel sides turning into a curved arch). The underside of the lid 15 may also be thickened so as to protrude into the chamber 5 and to displace liquid in the chamber 5 such that there is less risk of spillage when the lid 15 is removed. The thickness of the lid 15 may decrease towards the filter 4, i.e. angled, enabling the entire filter 4 to be visible. In addition, the lid 15 may be covered by a polystyrene ring seal (not shown), which should be removed in order to remove the lid 15.

A reinforcing tab may also be situated at some position on the outer side wall of the upper chamber 5, preferably at the top in egg collection mode. A tool can rest on the reinforcing tab to break the seal, enabling the seal to be levered off. Once broken, the seal ring can be peeled off. The seal ring may be rigid (and brittle) so comes off in one piece. When the reinforcing tab is at the highest point of the chamber (in collection mode), the air outlet may preferably be positioned at the upper most part of the chamber, beneath the reinforcing tab (in viewing mode).

In addition, the upper surface of the lid 15 may comprise a tab which functions as a handle to remove the lid 15. The tab may preferably be positioned so as not to block view of the chamber 5, e.g. directly above the baffle (viewing mode). It could also be positioned in the area of the upper chamber 5 above the baffle (in collection mode), preferably to the right or left of the centre.

Advantages of the Egg Chamber

The egg chamber has a number of advantages when compared to the prior art;

- The temperature of the egg is controlled at all times (increased cell viability)
- The eggs remain in an enclosed fluid environment at all times, enabling a stable pH to be maintained and minimising the risk of contamination and/or exposure to volatile organic compounds (VOCs)
- The egg collection process is continuous, i.e. there is no need to transfer from test tube to test tube. All eggs are collected in the one enclosed chamber. (less labour intensive, minimizes contamination risk, prevents heat loss)
- Eggs are automatically cleaned (separated from blood in follicular fluid) within the chamber, and are presented to the embryologist in a clear fluid, and can therefore be easily identified. (Saves embryologist time, less cooling, minimizes contamination risk).
- The chamber is only opened once in the embryology laboratory (ideally within an isolator), when the embryologist is ready to pick the eggs out and place them in culture medium under oil (minimizes contamination risk).
- The eggs can be maintained in the enclosed airtight chamber in an incubator after retrieval. Thus the clinical procedure of egg collection and the embryology process of identification of the eggs become independent. This is a more efficient use of both clinical and embryologist's time and allows flexibility in the location of lab and clinic.
- The chamber can be used to replace the follicular fluid with a buffered medium (or saline) providing an osmotically and pH stable environment for the eggs.

From the clinician's perspective the system works much in the same way as the current system, i.e. the existing needle and tubing collection can be used, the chamber can be transparent, and the aspirated fluid can be visible in the new system much like it is in the current.

From the embryologist's perspective, existing equipment is used (microscopes, hood etc.), and the dish is a similar size to that used already. In some embodiments the eggs might sit on a different base from that of the existing method, but will appear the same under the microscope and will be easy to identify.

The dish may be similar in size/shape to current petri dishes used during oocyte selection and cleaning, and large enough to provide optimum filter area. In addition, the egg chamber may have application in the veterinary IVF market. Since veterinary IVF is often carried out in a poorly controlled environment, the advantages of the egg chamber would be extremely desirable.

Manufacture of the Egg Chamber

In a preferred method of manufacturing, an egg chamber is made from the following components;

- First internal chamber—injection moulded polystyrene
- Second internal chamber—injection moulded polystyrene
- Lid—injection moulded polystyrene
- Retaining ring—injection moulded polystyrene
- Air outlet connector—machined or injection moulded polystyrene
- Inlet and outlet connectors—injection moulded polystyrene
- Main filter mesh—60 µM nylon mesh
- Air outlet filter mesh—60 µM nylon mesh
- Gasket—Silicon gasket material The first internal chamber, second internal chamber, lid and retaining ring are manufactured from Polystyrene Luran HD-20 supplied by BASF. The purpose of the first internal chamber is to collect oocytes during an egg collection procedure. It also provides a vessel for embryologists to select and clean oocytes in once the collection procedure is complete. The first internal chamber is the first component in the assembly procedure. All other components mate to this chamber, the second internal chamber (or nose chamber) locates into the front, the gasket, lid and retaining ring are housed in the top and the air and inlet connectors locate into ports on the back wall.

The first internal chamber has the following features;

- Optically clear base for use under a microscope;
- Sacrificial welding bead around the top of the chamber;
- A gasket housing lip near the top of the side walls;
- Sliding/locating fit with the lid and gasket components;
- Push fit with the filter boss on the second internal chamber/nose component;
- Push fit with the air and inlet connections;
- Smooth surface around the front to give good contact when welding with the second internal chamber/nose component.

This second internal chamber channels flow from the first internal chamber through to an outlet connection. It interfaces with the main chamber through a boss extrusion which has a push fit into the main chamber. The boss extrusion provides a welding surface to mount the main filter mesh on. Once pushed into the main chamber an ultrasonic weld is used to seal the two together.

The second internal chamber has the following key features:

- Angled boss providing a welding surface for the filter mesh and location fit with the first internal chamber;
- Sacrificial welding bead around inlet to the second internal chamber/nose chamber to weld with the filter mesh;
- Sacrificial welding bead around the base of the boss extrude to weld with the first chamber;
- Push fit with the outlet connector;
- Flat contact area around the outlet connector hole allowing access for the welding sonitrode.

The lid is inserted into the top of the main chamber to sandwich the gasket and make a sealed device. Close to the rear of the lid is a baffle. This is used to reduce turbulence in the flow and aid distribution across the filter mesh. The baffle has a slight angle to the centre of the chamber which acts as a channel for 'drip catching' as the lid is removed. The lid is a particularly thick sectioned component protruding deep into the main chamber. This protrusion reduces the liquid volume of the main chamber, leaving a desirable working volume of fluid once the lid is removed. A tab protrudes from the top of the lid which provides a picking point allowing users to lift the lid from the main chamber.

The lid component has the following key features:
Location fit with the main chamber;
Smooth, flat surface finish to sandwich the gasket, making a seal;
Optically clear to allow users to view the chamber contents;
A clearance of at least 1 mm between the bottom of the baffle and the chamber base.

The retaining ring must provide a retaining weld with the top of the main chamber to sandwich the silicone gasket and generate a sealed device. The ring has a locating ridge around its edge which positions it over the main chamber, aligning it with the sacrificial welding bead.

The retaining ring has the following key features:
Sliding fit with the main chamber;
Structural integrity to compress the silicone gasket.

The air outlet connector is preferably machined from Polystyrene Rexolite 1422. This could be injection moulded from Polystyrene Luran HD-20.

The air outlet connector must have two sacrificial welding beads, one to weld a filter mesh to and the second to weld the connector into the first internal chamber. This air outlet connector provides interface with the tubing components which connect the pumps, valves and needle to the chamber. Tubing locates and is forced over the male tubing connector to make a seal.

The air outlet connector has the following key features:
Tubing connector (barbed or micro luer slip) to seal with standard tubing material as used in the IVF industry;
Tubing connector to seal with tubing of 1 mm ID and 2 mm OD;
Push fit with the first internal chamber;
Sacrificial welding bead to weld a filter mesh over the connector;
Sacrificial welding bead to weld the connector into the first internal chamber.

The inlet/outlet connector must have a sacrificial welding bead to weld the connector into the first internal chamber (inlet) and the second internal chamber (outlet). This inlet/outlet connector provides an interface with the tubing components which connect the pumps, valves and needle to the chamber. Tubing locates and is forced over the male tubing connector to make a seal.

The inlet/outlet connector has the following key features:
Tubing connector (barbed or micro luer slip) to seal with standard tubing material as used in the IVF industry;
Tubing connector to seal with tubing of 1 mm ID and 2 mm OD;
Push fit with the main and nose chambers;
Sacrificial welding bead to weld the connector into the first and second internal chambers.

The inlet/outlet connectors are preferably machined from Polystyrene Rexolite 1422. These could be injection moulded in Polystyrene Luran HD-20 either individually or as part of the first internal chamber and nose chamber.

The air outlet filter mesh is manufactured from a Nylon mesh supplied by Millipore with a pore size of 60 μm. The air outlet filter mesh provides a filtration area of 1.13 $mm^2$. The filter is welded onto the air inlet connector which is then welded into the main chamber to create a seal. This filter acts as a failsafe to prevent eggs from escaping through the air outlet.

The air outlet filter mesh has the following key features:
Manufactured from Nylon;
60 μm filter pore size.

The silicone gasket is manufactured from medical grade silicone and is fitted over the protruding portion of the lid component. As the lid is inserted into the main chamber the gasket is sandwiched. As the retaining ring is then welded in place the gasket is then compressed and generates a seal on the main chamber.

The silicone gasket has the following key features:
Location fit with the protruding portion of the lid component;
0.5-1 mm thickness to provide the required compression to make a seal.

Components are manufactured in batches on injection moulding or CNC machinery. Each injection moulded component has its own individual mould which is fitted into the moulding machine. BASF supplied polystyrene Luran HD-20 in bulk granulated form is fed into the machine's input hopper. Moulding parameters are then applied for individual components and the process runs automatically, finished components are ejected from the machine and collected in bulk containers before being bagged individually. Each CNC machined component is manufactured running a set machining program, finished components are then collected, ultrasonically washed and bagged. Each individual component then comes to an assembly area and is assembled as shown in FIG. 10.

Ultrasonic welding of components is used to assemble the chambers. This negates any need for the use of harmful solvents when bonding components. A standard ultrasonic welder is used with a range of sonitrodes depending on the required geometry of the weld.

The manufacturing process is carried out in a minimum grade 7 clean room environment wherever possible.

Fluid Pump System

A fluid pump system 100 suitable for IVF egg collection is described referring to FIGS. 7 and 11 to 15. FIG. 11 shows a schematic of a preferred embodiment of the fluid pump system of the egg collection system described in FIG. 7 A-G. The preferred embodiment of the fluid pump system 100 comprises a first peristaltic pump 102, a second peristaltic pump 104, a heated saline reservoir 106, a waste reservoir 108, an egg collection chamber 110 with a heated stage, an extraction port 112 coupleable to, for example, a needle 114 and a controller (not shown in the schematic).

The fluid pump system 100 may contain a removable container (Chamber house) to house the chamber. The rear side of the chamber house that makes the majority of contact with the fluid pump system 100 may be made of aluminium; this is to allow thermal conduction of heat from heated stage on the pump to the chamber. The front of the chamber house may have a lid made of clear Perspex material in order to allow the operator to visually inspect the collection of fluid into the chamber. The chamber slots into the chamber housing and the Perspex lid is closed. The chamber housing slides into two lips of the fluid pump system 100 for operational purposes.

The inlet port 116 of the first peristaltic pump 102 is fluidly connected to the heated saline reservoir 106 via a first tubing 118, and the outlet port 120 is fluidly connected to a fluid junction 122 via a second tubing 124. The extraction port 112 (and needle 114) is fluidly connected to the fluid junction 122 via a third tubing 126 and the fluid junction 122 is further fluidly connected to an inlet port 128 of the egg collection chamber 110 via a fourth tubing 130. The outlet port 132 of the second peristaltic pump 104 is fluidly connected to the waste reservoir 108 via a fifth tubing 134. The inlet port 136 of the second peristaltic pump 104 is fluidly connected to a first outlet port 138 of the egg collection chamber 110 via a sixth tubing 140 and to a second outlet port 142 of the egg collection chamber 110 via a seventh tubing 144.

A first actuatable selector valve 202 is operatively coupled to the second tubing 124, a second actuatable selector valve 204 is operatively coupled to the fourth tubing 130, a third actuatable selector valve 206 is operatively coupled to the third tubing 126, a fourth actuatable selector valve 208 is operatively coupled to the seventh tubing 144 and a fifth actuatable selector valve 210 is operatively coupled to the sixth tubing 140.

The controller (not shown) is operatively coupled to at least the actuatable selector valves 202, 204, 206, 208 and 210, and to the first and second peristaltic pumps 102 and 104. The controller (not shown) may also be operatively coupled to any controllable heater (not shown) of the egg collection chamber 110 and the heated saline reservoir 106. In addition, the controller (not shown) may also be operatively coupled to any sensor integrated within the fluid pump system 100. The sensors may be adapted to determine physical properties within the fluid pump system 100, such as, for example, fluid flow rate, fluid temperature and/or ambient temperature.

The controller may be programmed to run predetermined sequences of selector valve 202 to 210 actuation and operation of the first and second peristaltic fluid pump 102 and 104. For example, the controller (not shown) may be configured to first run a "Fill Chamber" sequence as shown in FIG. 12A. Here, the third and fourth selector valves 206, 208 are actuated (i.e. closed) so as to form a fluid path from the heated saline reservoir 106 through the egg collection chamber 110 via the sixth tubing 140 and the second peristaltic pump 104 to the waste reservoir 108. Both pumps 102 and 104 are activated to move fluid from the heated saline reservoir 106 into the egg collection chamber 110 and through to the waste reservoir 108, filling the egg collection chamber 110 with heated saline fluid in the process.

Figure 12B:
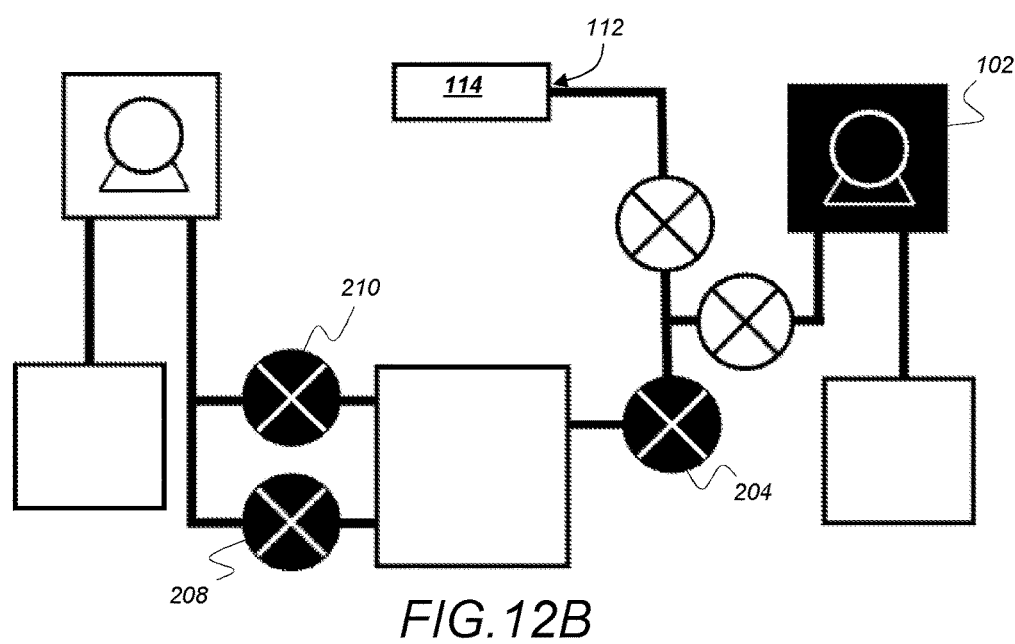
Figure 13:
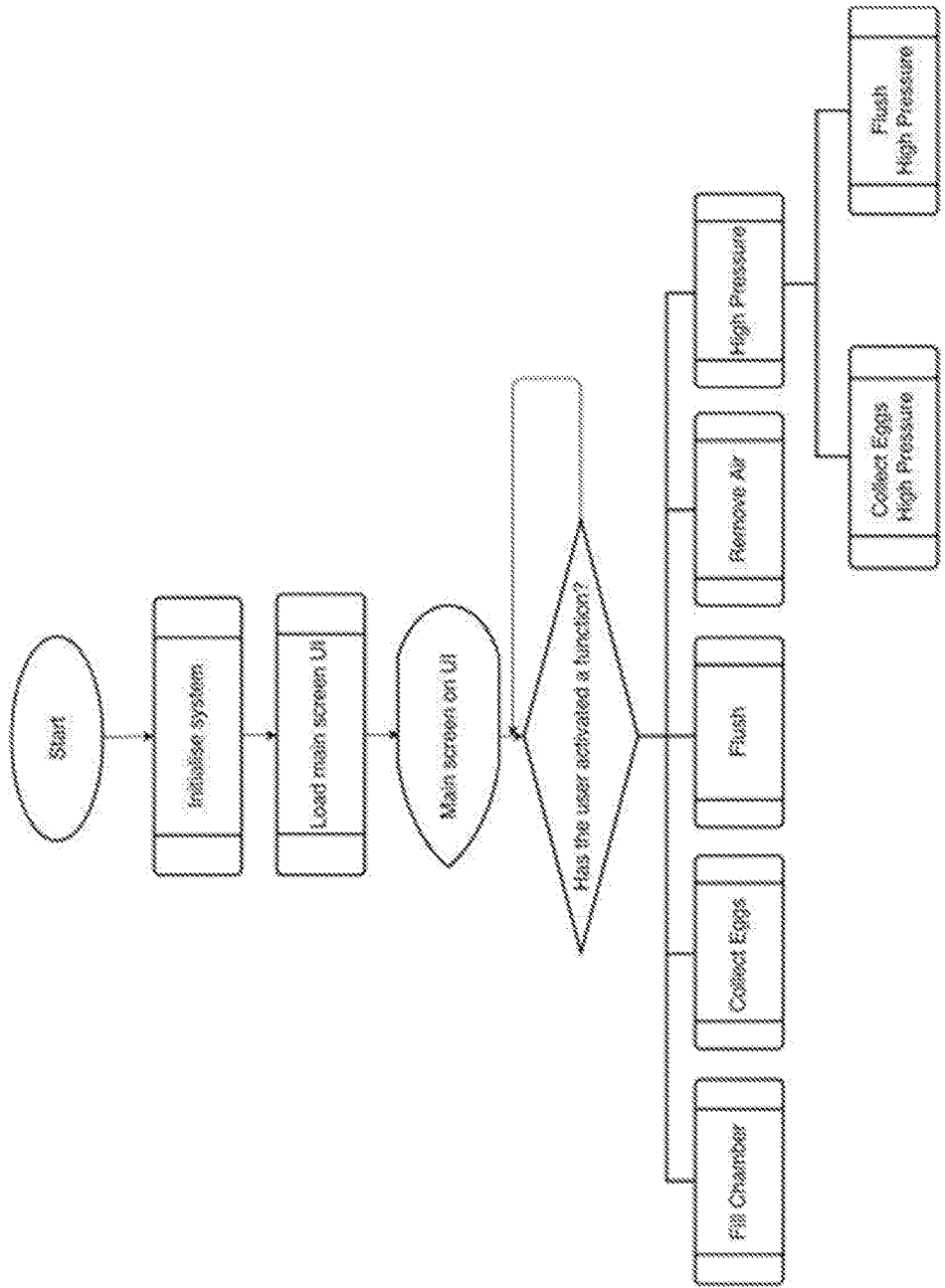

After the "Fill Chamber" sequence, the controller runs the "Flush" sequence as depicted in FIG. 12B. In this sequence the second, fourth and fifth selector valves 204, 208, 210 are closed forming a fluid path from the heated saline reservoir to the extraction port 112 and needle 114. The first peristaltic pump 102 is activated to flush saline fluid out of the extraction port 112 and needle 114. The fluid connection to the egg collection chamber 110 is blocked off.

Figure 12C:
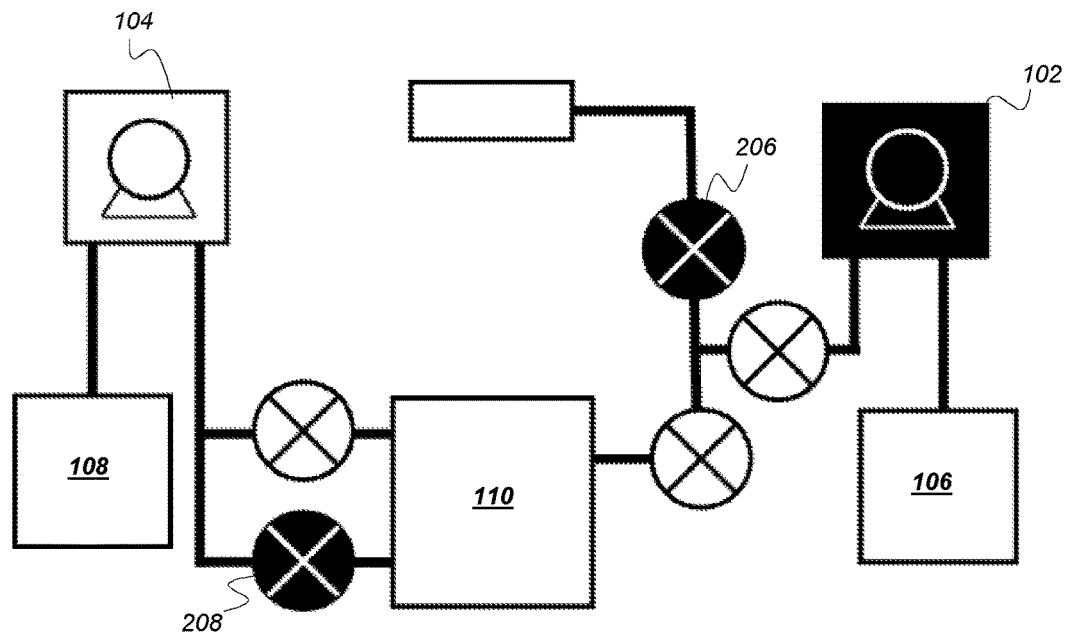

After the system has been flushed, the controller may run a "Remove Air" sequence either automatically after the "Flush" sequence or once triggered manually by, for example, an external actuator (e.g. a foot pedal). As shown in FIG. 12C, the third and fourth selector valve 206, 208 is closed forming a fluid path from the heated saline reservoir 106 through the egg collection chamber 110 and into the sixth tubing 140. The first peristaltic pump 102 is activated to add a controlled amount of saline fluid to be added to the egg collection chamber so as to remove any residue air that may have been trapped in the egg collection chamber 110 during the "Fill Chamber" sequence.

Figure 12D:
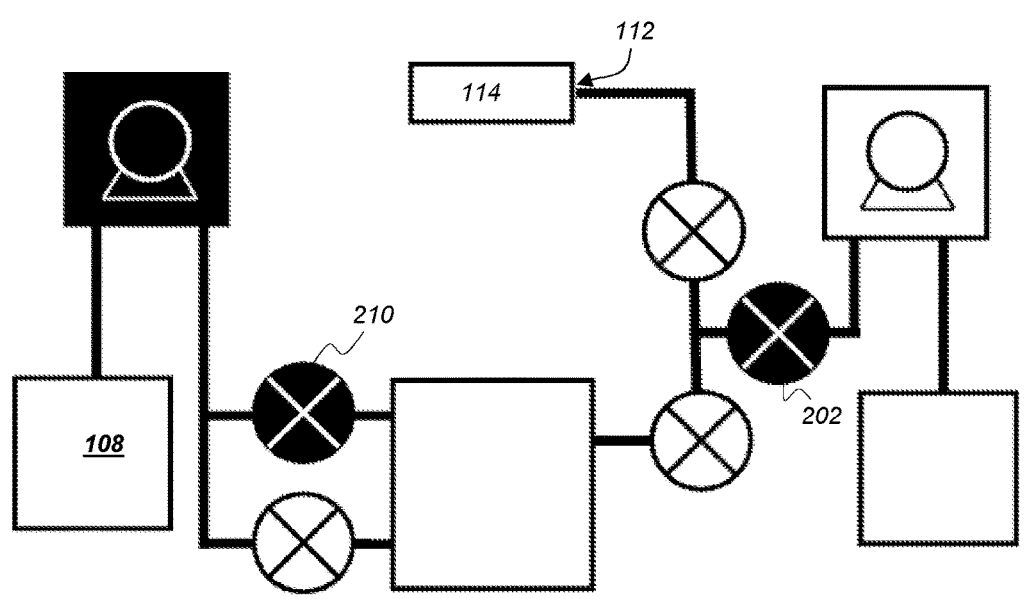

The fluid pump system is now 'primed' and the "Collect Eggs" sequence is started by the controller, either automatically or when triggered manually by an external actuator (not shown), such as, for example, a foot pedal. As shown in FIG. 12D, the first and fifth selector valves 202, 210 are closed forming a fluid path from the extraction port 112 and needle 114 into the egg collection chamber 110, and a fluid path from the egg collection chamber 110 into the waste reservoir 108 via the second peristaltic pump 104. The second peristaltic pump 104 is activated so as to move fluid from the needle through the egg collection chamber. Any eggs extracted will be captured in the egg collection chamber 110. Excessive fluid is moved into the waste reservoir 108. As discussed previously, the egg collection chamber is configured not to allow any eggs to be moved into the waste reservoir 108.

A "High Pressure" function executable by the controller allows operating, for example, the "Flush" sequence and the "Collect Eggs" sequence with the pumps 102, 104 running at a higher flow rate. However, the speeds at which each one of the two pumps 102, 104 operate may be adjustable to any suitable speed.

Referring now to FIG. 13, a high-level main process flow schematic shows the command and sequence structure of the fluid pump system 100 executable through the controller (not shown). Once the system 100 is powered up, an automatic initialisation sequence is executed, where the controller establishes communication with all actuators (i.e. selector valves, pumps) and sensors (if available) as well as user interface and the control hardware of the controller.

Figure 14A:
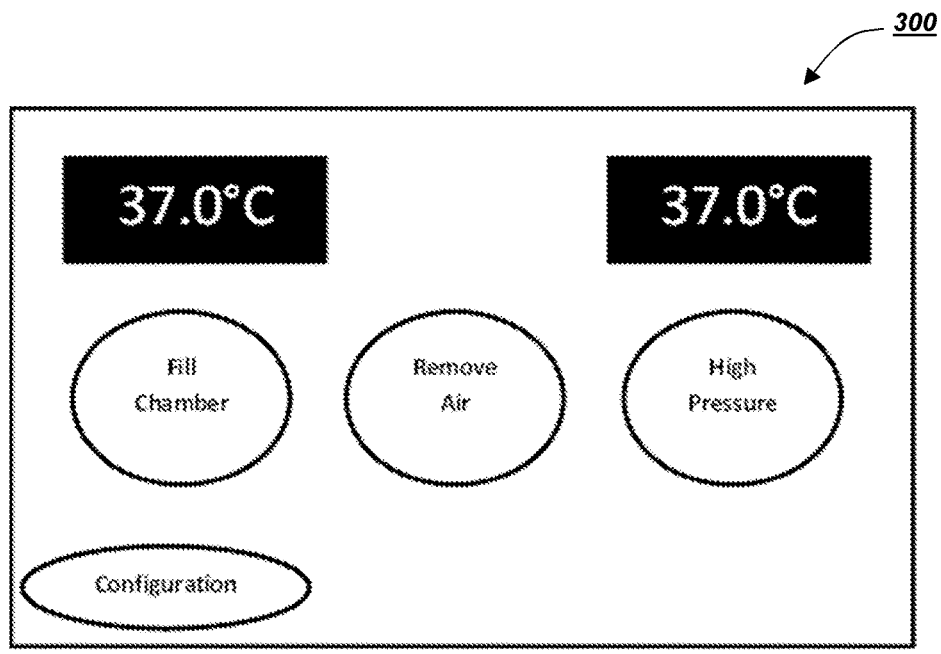
Figure 14B:
Figure 14C:
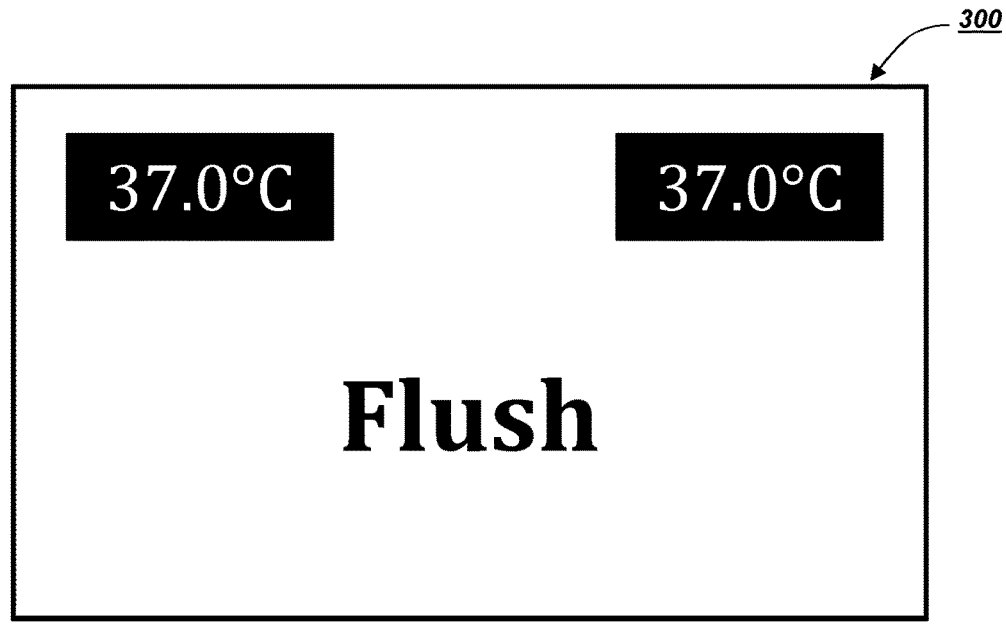
Figure 14D:
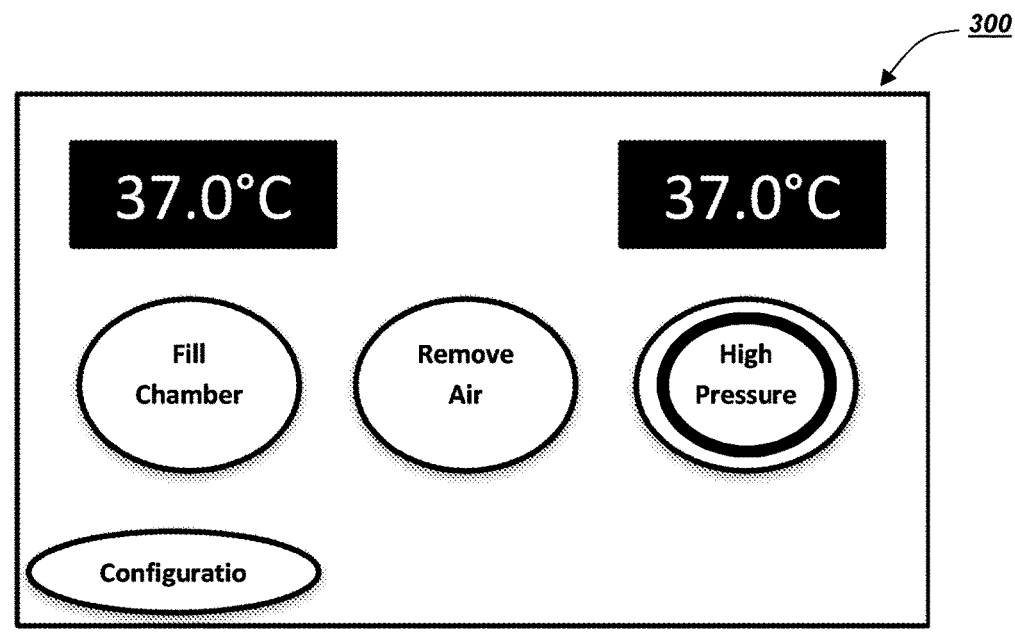
Figure 14E:
Figure 15:
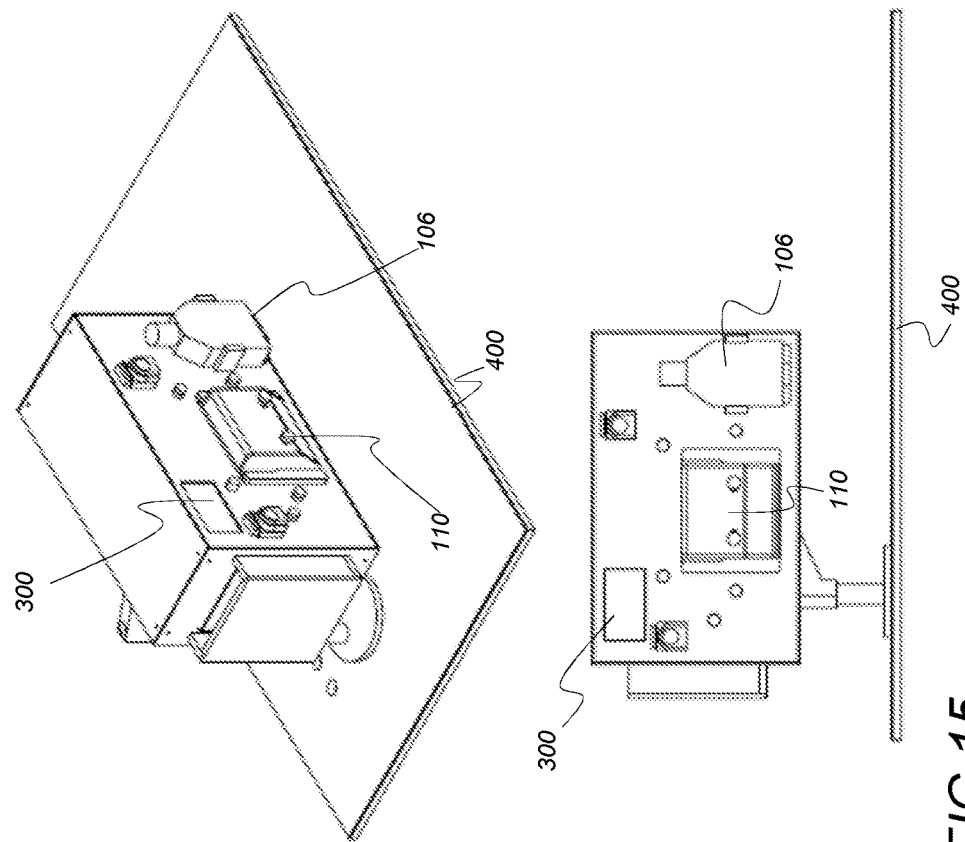
Figure 15:
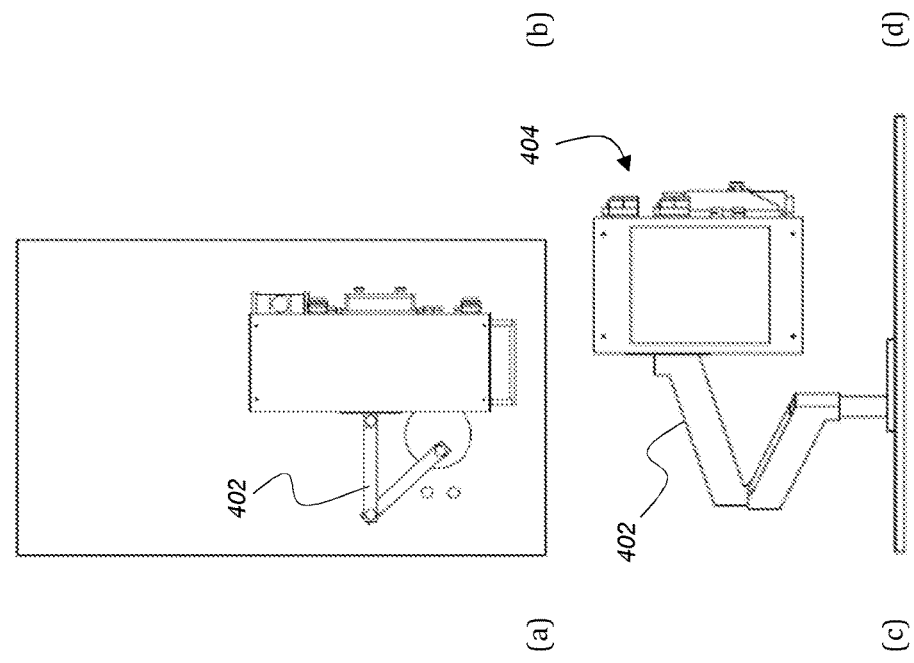

A typical user interface 300 of the controller is shown in FIG. 14A-E. The user interface may be a touch screen that allows the user to access all operation modes. After the initial power up a screen layout such as shown in FIG. 14A may be displayed to the user. In this state the processor of the controller executes a waiting loop until a function is selected by the user. The user interface shown in FIG. 14A also provides information on the current temperatures measured in the heated saline reservoir 106 and the egg collection chamber 110.

FIGS. 14B-E show the user interface display at the different sequences. Each sequence may be initiated through an external actuator (e.g. foot pedal), or, alternatively, the sequences may be executed automatically by the pre-programmed controller. Preferably, the user interface is 'locked' until each sequence is completed.

Also, different background colours may be used to indicate the current state of operation of the fluid pump system 100. For example, during the initiation sequence, the screen background may be blue, during the "Collect Eggs" sequence, the screen background may be green, during the "Flush" sequence, the screen background may be orange and the "High Pressure" sequence may be indicated by a red screen background.

FIG. 15 depicts an example of a design of the fluid pump system 100 in different views, i.e. (a) top view, (b) perspective view, (c) side view and (d) front view. In this embodiment, the fluid pump system 100 is coupled to a table top 400 via a movable arm 402. The front panel 404 comprises the egg collection chamber 110, the saline reservoir 106 and a user interface display 300.

It will be appreciated by persons skilled in the art that the above embodiment(s) have been described by way of example only and not in any limitative sense, and that various alterations and modifications are possible without departing from the scope of the invention as defined by the appended claims.

The invention claimed is:

1. An egg chamber in a form of a vessel which can be made airtight, comprising:
   at least one side wall;
   a planar upper wall and a planar lower wall, at least a portion of said planar upper wall being transparent and at least a portion of said planar lower wall being light permeable;
   a first inlet which is adapted to be sealed;
   a first outlet which is adapted to be sealed; and a filter with a pore size of greater than 10 microns but small enough to retain an ovum disposed within the vessel between said first inlet and said first outlet and configured to bisect the vessel into a first internal chamber and a second internal chamber, wherein said filter extends at an angle between 45° and 90° degrees from said planar lower wall, wherein when said egg chamber is in an egg collection orientation said filter is in a substantially horizontal orientation while said lower planar wall is substantially vertical.

2. The egg chamber of claim 1 wherein said first inlet or said first outlet is self-sealing.

3. The egg chamber of claim 1 which is provided with detachable tubing attached to one or more of said first inlet or said first outlet.

4. The egg chamber of claim 3 wherein the detachable tubing is adapted to connect a needle and said egg chamber, and a reservoir and said egg chamber are insulated to minimize heat loss.

5. The egg chamber of claim 1 wherein said filter extends perpendicular to said lower planar wall.

6. The egg chamber of claim 1 wherein said pore size of said filter is large enough that blood cells can pass through.

7. The egg chamber of claim 1 wherein said pore size of said filter is in a range between 20-100 μm, to allow blood cells to pass through but not oocytes.

8. The egg chamber of claim 1 wherein said pore size of said filter is in a range between 40 and 60 μm.

9. The egg chamber of claim 1 comprising a lid that forms part of said upper planar wall and a lip adjacent said lid covering a top 5-25% of said filter to discourage eggs from sticking.

10. The egg chamber of claim 1 wherein said planar lower wall is entirely translucent.

11. The egg chamber of claim 1 wherein said planar lower wall is entirely transparent.

12. The egg chamber of claim 1 wherein said planar upper wall is entirely transparent.

13. The egg chamber of claim 1 wherein said first inlet is positioned on the at least one side wall associated with said first internal chamber.

14. The egg chamber of claim 1 wherein said first inlet is positioned such that it is uppermost on said egg chamber when said egg chamber is in a collection orientation.

15. The egg chamber of claim 1 wherein said first outlet is positioned on the at least one side wall associated with said second internal chamber.

16. The egg chamber of claim 1 wherein said first outlet is positioned such that it is lowermost on said egg chamber when said egg chamber is in a collection orientation.

17. The egg chamber of claim 1 wherein the at least one side wall includes a first side portion and a second side portion that taper together in the direction from said first internal chamber to said second internal chamber.

18. The egg chamber of claim 1 wherein where said planar lower wall meets the at least one side wall in said first internal chamber, there is an incline.

19. The egg chamber of claim 1 wherein said egg chamber further comprises an air sensor adapted to detect if any air is aspirated into said first internal chamber.

20. The egg chamber of claim 1 wherein said egg chamber further comprises an air outlet port.

21. The egg chamber of claim 1 wherein said lower planar wall of an upper said first internal chamber is provided with visual markings.

22. The egg chamber of claim 1 wherein a flow directing device or flow restriction device is positioned in an upper said first internal chamber.

23. The egg chamber of claim 1 comprising a baffle positioned in said first internal chamber.

24. The egg chamber of claim 23 wherein said baffle is attached to said planar upper wall.

25. The egg chamber of claim 24 wherein said baffle is integral to said planar upper wall and protrudes downwards from a lower surface of said planar upper wall into said egg chamber in a viewing orientation.

26. The egg chamber of claim 23 wherein said baffle is positioned between said first inlet port and said filter.

27. The egg chamber of claim 23 wherein said baffle is linear.

28. The egg chamber of claim 27 wherein said baffle is at 90-95° to an attached part of said egg chamber.

29. The egg chamber of claim 27 wherein the at least one side wall includes a first side wall portion and a second side wall portion, wherein there is a space of 1 mm to 3 mm between each end of said linear baffle and said respective first side wall portion and said second side wall portion.

30. The egg chamber of claim 27 wherein said linear baffle is between 1 mm and 5 mm wide.

31. The egg chamber of claim 23 wherein there is a space of about 1-5 mm between said baffle and said planar lower wall.

32. The egg chamber of claim 23, wherein said baffle is v-shaped.

33. The egg chamber of claim 1 comprising corners where two internal planes meet having a radius >0.05 mm and <10 mm.

34. The egg chamber of claim 1 comprising a lid or access point that is adapted to be removed.

35. The egg chamber of claim 34 wherein said lid is a screw thread type lid which is adapted to be removed.

36. The egg chamber of claim 34 wherein said lid is a friction push fit lid.

37. The egg chamber of claim 34 wherein said lid is a heat sealable lid.

38. The egg chamber of claim 34 wherein said lid is a location fitting lid which is mechanically pushed and retained onto a gasket, compressing said gasket so as to make a seal.

39. The egg chamber of claim 1 comprising visual or mechanical means for seeing if said egg chamber has been tampered with, used or opened.

40. The egg chamber of claim 1 wherein another filter covers said first outlet on an inner side of said egg chamber.

41. The egg chamber of claim 1 which is stackable for ease of storage.

42. A method of collecting eggs or ova from an animal, using said egg chamber of claim 1 comprising the steps of:
    obtaining said egg chamber with a first tube connected to said egg chamber via said first inlet, said first tube being associated with a needle, and a second tube connected via said first outlet;
    priming said egg chamber by filling said egg chamber, said first tube, said second tube and said needle with a liquid;
    positioning said egg chamber in the egg collection orientation whereby said first internal chamber is disposed above said second internal chamber;
    aspirating follicular fluid through said needle into said egg chamber, such that the follicular fluid is drawn through said filter disposed within said egg chamber thus retaining eggs in said first internal chamber of said egg chamber;

removing the follicular fluid from said second internal chamber through said first outlet; and positioning said egg chamber in an inspection orientation in which said filter is in a substantially vertical orientation while said lower planar wall is substantially horizontal.

43. An egg collection system comprising said egg chamber of claim 1 and a pump station; said egg chamber connected via said first inlet to a first tube and a needle and further connected to a second tube via said first outlet; said pump station comprising a first priming pump associated with a sterile liquid reservoir and said first tube and a second aspirating pump associated with said second tube and adapted to draw fluid through from said needle, via said egg chamber to said second tube.

44. The egg collection system of claim 43 wherein said second tube is associated with a waste reservoir.

45. The egg collection system of claim 43 wherein said first priming pump is a peristaltic pump.

46. The egg collection system of claim 43 wherein both said first priming pump and said second aspirating pump are peristaltic pumps.

47. The egg collection system of claim 43 wherein said second aspirating pump is a vacuum pump.

48. The egg collection system of claim 43 wherein said egg chamber is received within a heated housing.

49. The egg collection system of claim 48 wherein at least part of said heated housing allows said egg chamber to be viewed.

50. The egg collection system of claim 48 wherein said heated housing is adapted to hold said egg chamber in the collection orientation.

51. The egg chamber of claim 1, wherein said filter extends at an angle between 70° and 90° from said planar lower wall.

52. An egg collection vessel, comprising:

at least one side wall, an upper wall and a lower planar wall, wherein at least a portion of said upper wall is transparent and at least a portion of said lower planar wall is light permeable;

wherein said upper wall comprises a removable lid;

an inlet and an outlet;

a filter with a pore size of greater than 10 microns but small enough to retain an ovum disposed between said inlet and said outlet and configured to separate the egg collection vessel into a first internal chamber and a second internal chamber;

wherein said inlet leads to said first internal chamber and said outlet leads from said second internal chamber;

wherein when said egg collection vessel is disposed in an egg collection orientation said first internal chamber is disposed above said second internal chamber, said filter is in a substantially horizontal orientation while said lower planar wall is substantially vertical and said filter permits passage of fluid while retaining eggs in said first internal chamber; and wherein when said egg collection vessel is disposed in an egg inspection orientation said filter is in a substantially vertical orientation and said lower planar wall is substantially horizontal, permitting a view by a person from above the egg collection vessel of eggs located in said first internal chamber.

53. The egg collection vessel of claim 52 wherein said filter extends at an angle ranging from 45 to 90 degrees relative to said lower planar wall.

* * * * *